(12) United States Patent
Berry et al.

(10) Patent No.: US 11,439,454 B2
(45) Date of Patent: Sep. 13, 2022

(54) TELEOPERATED SURGICAL SYSTEM EQUIPMENT WITH USER INTERFACE

(71) Applicant: INTUITIVE SURGICAL OPERATIONS, INC., Sunnyvale, CA (US)

(72) Inventors: Julie L. Berry, San Jose, CA (US); Paul W. Mohr, Mountain View, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 56 days.

(21) Appl. No.: 16/221,981

(22) Filed: Dec. 17, 2018

(65) Prior Publication Data

US 2019/0192211 A1 Jun. 27, 2019

Related U.S. Application Data

(63) Continuation of application No. 14/659,827, filed on Mar. 17, 2015, now Pat. No. 10,166,061.
(Continued)

(51) Int. Cl.
*A61B 34/00* (2016.01)
*A61B 18/12* (2006.01)
(Continued)

(52) U.S. Cl.
CPC .......... *A61B 18/12* (2013.01); *A61B 18/1206* (2013.01); *A61B 34/25* (2016.02);
(Continued)

(58) Field of Classification Search
CPC ..... A61B 18/12; A61B 18/1206; A61B 34/26; A61B 34/30; A61B 34/74
See application file for complete search history.

(56) References Cited

U.S. PATENT DOCUMENTS

| 6,040,537 A | 3/2000 | McClintock |
| 6,074,388 A | 6/2000 | Tockweiler et al. |

(Continued)

FOREIGN PATENT DOCUMENTS

| CN | 101297760 A | 11/2008 |
| WO | WO-9749340 A1 | 12/1997 |

(Continued)

OTHER PUBLICATIONS 802.3af-2003—IEEE Standard for Information Technology—Telecommunications and Information Exchange Between Systems—Local and Metropolitan Area Networks—Specific Requirements [online], 2003, Current Version Jul. 22, 2003, DOI 10.1109/IEEESTD2003.94284, Persistent Link: http://ieeexplore.ieee.org/servlet/opac?punumber=8612.

(Continued)

*Primary Examiner* — Eric D. Bertram
(74) *Attorney, Agent, or Firm* — Jones Robb, PLLC

(57) ABSTRACT

A method comprises simultaneously presenting on a display a plurality of graphical screen sections, each graphical screen section comprising adjustable control settings. The plurality of graphical screen sections respectively align with a plurality of connector ports, and each connector port is configured to be operably coupled with a surgical instrument.

18 Claims, 14 Drawing Sheets

Related U.S. Application Data

(60) Provisional application No. 61/954,118, filed on Mar. 17, 2014.

(51) Int. Cl.
*G06F 3/04847* (2022.01)
*G06F 3/0488* (2022.01)
*G06F 3/033* (2013.01)
*G06F 3/04817* (2022.01)
*A61B 34/30* (2016.01)

(52) U.S. Cl.
CPC ............ *A61B 34/74* (2016.02); *G06F 3/0334* (2013.01); *G06F 3/0488* (2013.01); *G06F 3/04817* (2013.01); *G06F 3/04847* (2013.01); *A61B 34/30* (2016.02); *G06F 2203/0383* (2013.01); *G06F 2203/04803* (2013.01)

(56) References Cited

U.S. PATENT DOCUMENTS

| | | | |
|---|---|---|---|
| 6,113,596 A | 9/2000 | Hooven et al. | |
| 6,493,608 B1 | 12/2002 | Niemeyer et al. | |
| 6,522,906 B1 | 2/2003 | Salisbury, Jr. et al. | |
| 6,840,938 B1 | 1/2005 | Morley et al. | |
| 6,849,071 B2 | 2/2005 | Whitman et al. | |
| 6,994,708 B2 | 2/2006 | Manzo | |
| D517,501 S | 3/2006 | Kotyk | |
| 7,122,032 B2 | 10/2006 | Shinmura et al. | |
| 7,217,269 B2* | 5/2007 | El-Galley | A61B 18/1402 606/34 |
| 7,320,700 B2 | 1/2008 | Cooper et al. | |
| 7,353,068 B2 | 4/2008 | Tanaka et al. | |
| 7,367,973 B2 | 5/2008 | Manzo et al. | |
| 7,379,563 B2 | 5/2008 | Shamaie | |
| 7,428,439 B1 | 9/2008 | Reynolds et al. | |
| 7,594,912 B2 | 9/2009 | Cooper et al. | |
| 8,120,301 B2 | 2/2012 | Goldberg et al. | |
| 8,398,541 B2 | 3/2013 | Dimaio et al. | |
| 8,398,634 B2 | 3/2013 | Manzo et al. | |
| 8,418,073 B2 | 4/2013 | Mohr et al. | |
| 8,423,182 B2* | 4/2013 | Robinson | A61B 34/25 700/245 |
| 8,508,173 B2 | 8/2013 | Goldberg et al. | |
| 8,862,268 B2 | 10/2014 | Robinson et al. | |
| 10,166,061 B2* | 1/2019 | Berry | A61B 18/12 |
| 2003/0135204 A1 | 7/2003 | Lee et al. | |
| 2004/0167515 A1 | 8/2004 | Petersen et al. | |
| 2005/0008043 A1 | 1/2005 | Kousek et al. | |
| 2005/0080403 A1 | 4/2005 | Takahashi | |
| 2005/0251228 A1 | 11/2005 | Hamel | |
| 2006/0079889 A1 | 4/2006 | Scott et al. | |
| 2006/0087746 A1 | 4/2006 | Lipow | |
| 2006/0142657 A1 | 6/2006 | Quaid et al. | |
| 2007/0013336 A1 | 1/2007 | Nowlin et al. | |
| 2007/0016174 A1 | 1/2007 | Millman et al. | |
| 2007/0078539 A1 | 4/2007 | Kuhner et al. | |
| 2007/0167968 A1 | 7/2007 | Pandey | |
| 2007/0239172 A1 | 10/2007 | Lee et al. | |
| 2008/0046122 A1 | 2/2008 | Manzo et al. | |
| 2008/0125794 A1 | 5/2008 | Brock et al. | |
| 2008/0140158 A1 | 6/2008 | Hamel et al. | |
| 2008/0183189 A1 | 7/2008 | Teichman et al. | |
| 2008/0217564 A1 | 9/2008 | Beyar et al. | |
| 2008/0221473 A1 | 9/2008 | Calancie et al. | |
| 2008/0249547 A1 | 10/2008 | Dunn | |
| 2008/0262476 A1* | 10/2008 | Krause | A61B 17/32002 604/540 |
| 2008/0262538 A1 | 10/2008 | Danitz et al. | |
| 2008/0319313 A1 | 12/2008 | Boivin et al. | |
| 2009/0009492 A1 | 1/2009 | Gregorio et al. | |
| 2009/0012533 A1 | 1/2009 | Barbagli et al. | |
| 2009/0024142 A1 | 1/2009 | Ruiz | |
| 2009/0248007 A1* | 10/2009 | Falkenstein | A61B 90/90 606/33 |
| 2009/0248041 A1 | 10/2009 | Williams et al. | |
| 2009/0275940 A1* | 11/2009 | Malackowski | A61B 18/1233 606/42 |
| 2010/0082039 A1 | 4/2010 | Mohr et al. | |
| 2010/0234857 A1 | 9/2010 | Itkowitz et al. | |
| 2010/0305427 A1 | 12/2010 | Huber et al. | |
| 2011/0105898 A1* | 5/2011 | Guthart | A61B 34/35 600/437 |
| 2011/0238079 A1 | 9/2011 | Hannaford et al. | |
| 2011/0276058 A1 | 11/2011 | Choi et al. | |
| 2012/0046659 A1 | 2/2012 | Mueller | |
| 2013/0053840 A1* | 2/2013 | Krapohl | A61B 18/1445 606/33 |
| 2013/0274734 A1 | 10/2013 | Maass et al. | |
| 2013/0325031 A1 | 12/2013 | Schena et al. | |
| 2013/0325033 A1 | 12/2013 | Schena et al. | |
| 2014/0081455 A1 | 3/2014 | Goldberg et al. | |
| 2014/0128885 A1 | 5/2014 | Dachs, II et al. | |
| 2014/0128886 A1 | 5/2014 | Holop et al. | |
| 2014/0180272 A1 | 6/2014 | Dachs, II et al. | |
| 2014/0228833 A1* | 8/2014 | Friedrichs | A61B 18/042 606/27 |
| 2015/0012134 A1 | 1/2015 | Robinson et al. | |

FOREIGN PATENT DOCUMENTS

| | | |
|---|---|---|
| WO | WO-2008098085 A2 | 8/2008 |
| WO | WO-2010008126 A1 | 1/2010 |
| WO | WO-2011060139 A2 | 5/2011 |
| WO | WO-2011125007 A1 | 10/2011 |

OTHER PUBLICATIONS

Applied Surgical, Data Sheet for Gemini Operating Room, 1 Page, 2006; Internet: http://appliedsurgicalsolutions.com/.

Dugan, Kelli M., "Stepping Out," Birmingham Business Journal, Mar. 24, 2006, 2 pages; Internet: http://www.oadi.org/client%20news/Applied%20Surgical%20032406.pdf.

Erickson, J.R. et al., "Connectors Take on a new Life," Published Online on Sep. 1, 2012,< URL: http://www.designworlddonline.com/connectors-take-on-a-new-life/>.

Harris, William, "How Haptic Technology Works," downloaded Oct. 24, 2008, 6 pages; Internet: http://electronics.howstuffworks.com/gadgets/other-gadgets/haptic-technology4.htm.

International Search Report and Written Opinion for Application No. PCT/US2013/059938, dated Dec. 10, 2013, 11 pages.

International Search Report and Written Opinion for Application No. PCT/US2013/068059, dated Feb. 11, 2014, 18 pages.

Linemaster Switch Corp., Brochure titled "Precision Begins with a Linemaster Switch," 8 pages, 2000.

Linemaster Switch Corp., Data Sheet for Linemaster Wireless Linear Foot Switch, Lit-002 Rev D, 2 pages, downloaded Jan. 2, 2009; Internet: http://www.linemaster.com/media/DataSheets/LIT-002%20Rev%20Dsm.pdf.

Linemaster Switch Corp., Information sheet for Linemaster Infrared Wireless Linear Foot Switch, 2 pages, downloaded Jan. 2, 2009; Internet: http://www.linemaster.com/wirelesslinear.shtml.

Medical Design Magazine, "Wireless Footswitch Controls Several Surgical Devices," Nov. 1, 2006, 1 page; Internet: http://medicaldesign.com/engineering-prototyping/wireless_footswitch_controls/index.html.

PCT/US10/26307 International Search Report and Written Opinion of the International Searching Authority, dated Jul. 22, 2010, 9 pages.

Valley lab, "Force Triad", Energy platform, User's guide, 2006, 100 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

VIO 300 D "User Manual" Art. No. 80113-334, ERBE Elektromedizin GmbH, 2009, 170 pages.

VIO System, "Endo Cut I", MKT/5027/01 (Sep. 2006), ERBE, USA Incorporated Surgical systems, 2 pages.

(56) References Cited

OTHER PUBLICATIONS

VIO, the only system with a brain . . . and a pulse., MKT/5027/01 (Jul. 2004), ERBE, USA Incorporated Surgical systems, 5 pages.
Wikipedia, entry on "Ergonomics," printed Feb. 24, 2009 at 11:24 p.m., 10 pages; Internet: http://en.wikipedia.org/wiki/Ergonomics.

* cited by examiner

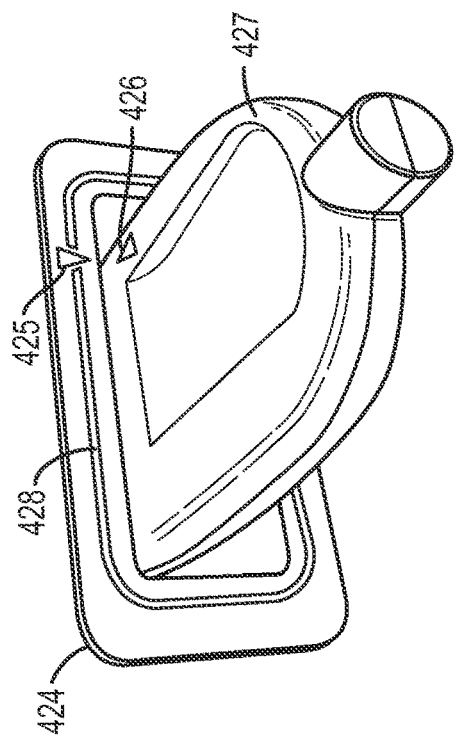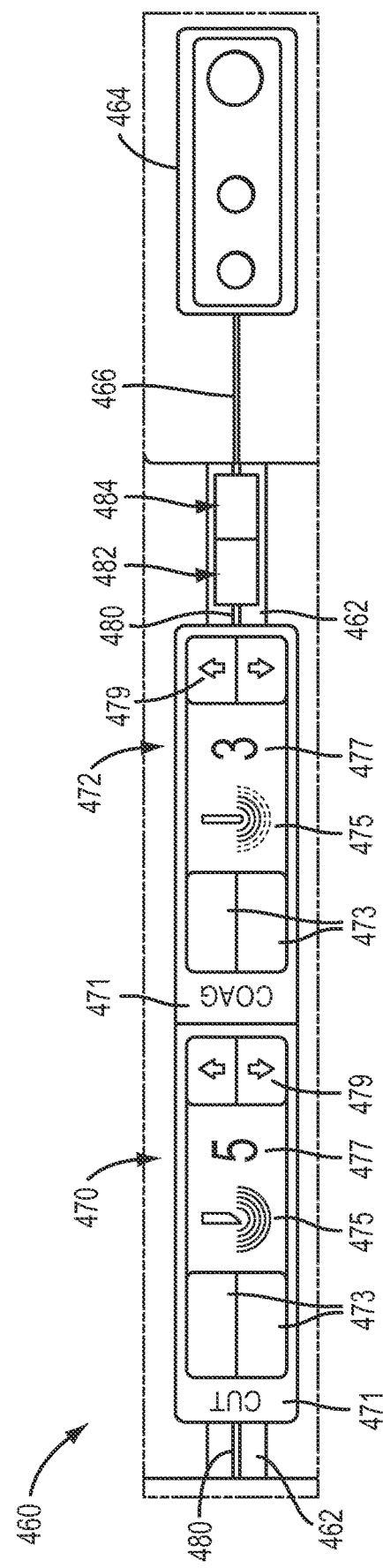

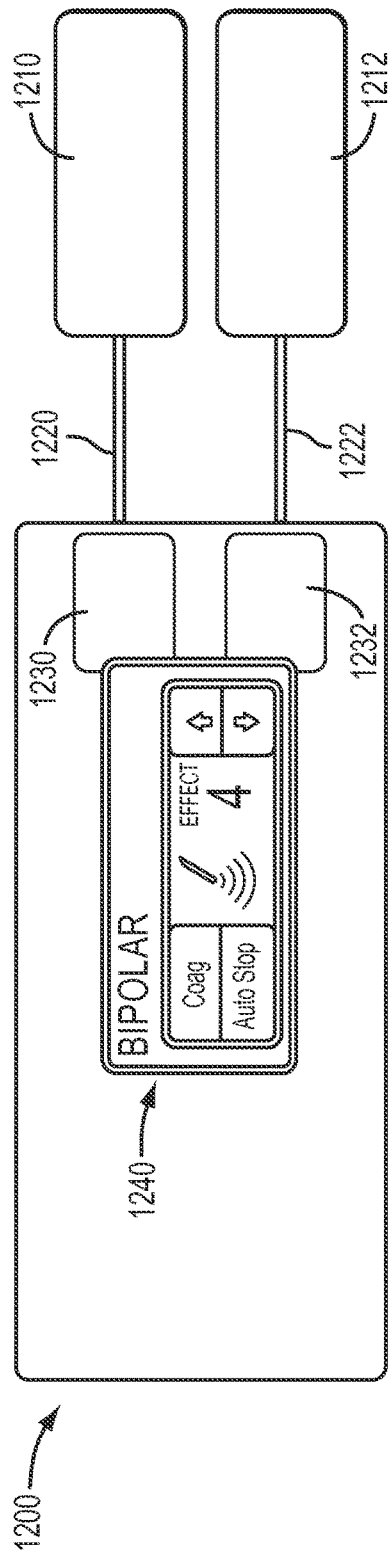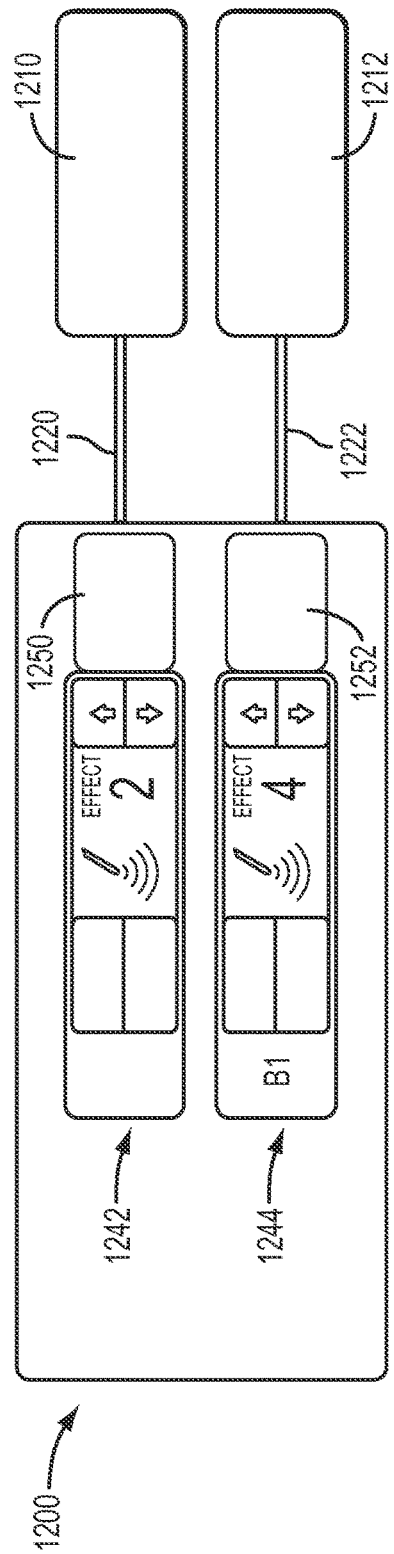

TELEOPERATED SURGICAL SYSTEM EQUIPMENT WITH USER INTERFACE

CROSS-REFERENCE TO RELATED APPLICATIONS

This application is a continuation of U.S. patent application Ser. No. 14/659,827, filed Mar. 17, 2015 (now U.S. Pat. No. 10,166,061), which claims priority to U.S. Provisional Application No. 61/954,118, filed Mar. 17, 2014, each of which is incorporated by reference herein in its entirety.

TECHNICAL FIELD

Aspects of the present disclosure relate to a user interface for surgical flux supply equipment, such as, for example, for use in a teleoperated surgical system.

INTRODUCTION

Some minimally invasive surgical techniques are performed remotely through the use of remotely controlled surgical instruments (also referred to as tools). In remotely controlled surgical systems, surgeons manipulate input devices at a surgeon console, and those inputs are passed to a patient side cart that interfaces with one or more remotely controlled surgical instruments. Based on the surgeon's inputs at the surgeon console, the one or more remotely controlled surgical instruments are actuated at the patient side cart to operate on the patient, thereby creating a master-slave control relationship between the surgeon console and the surgical instrument(s) at the patient side cart.

Teleoperated surgical systems may have one or more teleoperated (robotic) arms to which a plurality of surgical instruments may be coupled. One category of surgical instrument is electrosurgical instruments. Electrosurgical instruments may include monopolar electrosurgical instruments and bipolar electrosurgical instruments, as well as harmonic, laser, and ultrasonic instruments. Another category of surgical instruments includes tissue manipulation instruments which may have articulated end effectors (such as jaws, scissors, graspers, needle holders, micro dissectors, staple appliers, tackers, suction/irrigation instruments, clip appliers, or the like) or non-articulated end effectors (such as cutting blades, irrigators, catheters, suction orifices, or the like). One or more of these end effectors also may be configured with electrosurgical elements. While electrosurgical instruments and other instruments that deliver a flux (e.g., laser, irrigation, suction, etc.) are mechanically coupled to an arm to control their movements, they are also coupled to a flux supply unit, such as electrosurgical energy generating units (ESU's) in the case of an electrosurgical instrument. For instance, an ESU may generate and supply an electrosurgical flux energy to an electrosurgical instrument so that an electrosurgical energy may be applied to tissue at or near an end effector of the electrosurgical instrument. Other flux generating and supply units also may be coupled to an instrument that is configured to deliver a flux during the performance of a surgical procedure.

When connecting an electrosurgical or other surgical instrument configured to deliver flux to a flux supply unit, such as an ESU, there exists a need to provide a user with information about the connection between the instrument and the flux supply unit. There also exists a need to provide such information in a manner that is simple for a user to understand relatively quickly upon observation. Overall, there exists a need to improve upon user interfaces on flux supply units used to deliver flux to surgical instruments.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a flux supply unit for supplying a flux to a plurality of surgical instruments may comprise a plurality of connectors and a user control interface. The plurality of connectors may be configured to supply flux to the surgical instruments when the surgical instruments are operationally coupled to respective connectors. The user control interface may comprise a continuous display screen comprising a plurality of graphical display screen sections on the same display screen that display controls for surgical instruments operationally coupled to the plurality of connectors. The plurality of graphical display screen sections may display controls for different types of surgical instruments on the same continuous display screen. The plurality of graphical display screen sections may be arranged relative to the plurality of connectors to visually couple respective graphical display screen sections and connectors to indicate respective associations of the graphical display screen sections with the connectors.

In accordance with another exemplary embodiment, a method of displaying information for a flux supply device of a teleoperated surgical system may comprise displaying the information in a plurality of graphical display screen sections on the same display screen of a continuous display screen. The graphical display screen sections may display controls for surgical instruments operationally coupled to a plurality of connectors. The controls may include controls for different types of surgical instruments. The displaying the information may comprise displaying the information in the graphical display screen sections that are visually coupled to the connectors to indicate an association between the graphical display screen sections and connectors.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

FIG. 5 is a perspective view of an exemplary embodiment of a connection for an electrosurgical instrument connected to a connector of a module of an ESU.

FIG. 6 is a front view of a module of an ESU, according to an exemplary embodiment.

FIG. 26 is a front view of an exemplary embodiment of a module of an ESU prior to connection with a specialized instrument.

FIG. 27 shows the module of FIG. 27 after connection with a specialized instrument.

DETAILED DESCRIPTION

Figure 1:
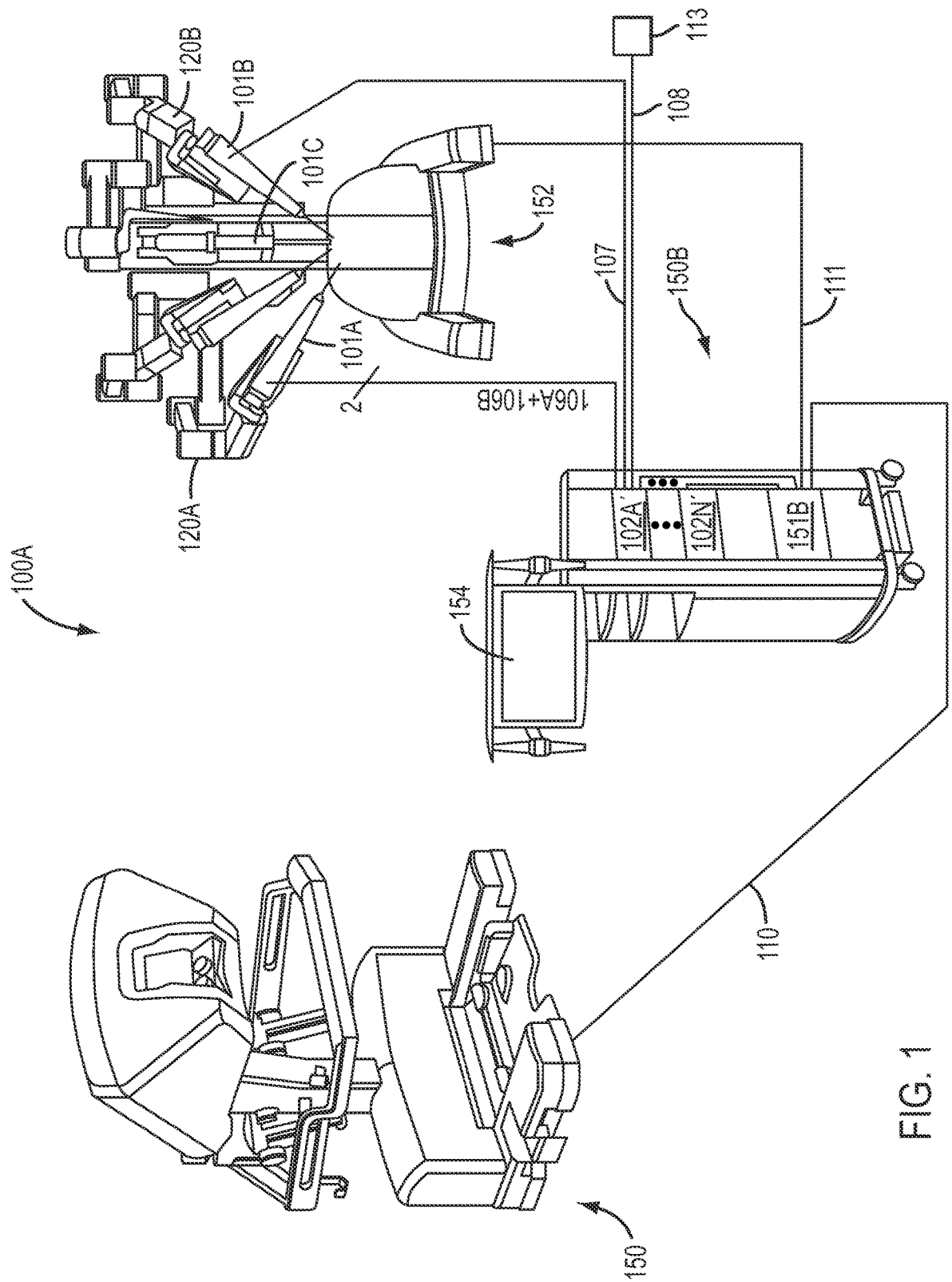
FIG. 1 is a diagrammatic view of a teleoperated surgical system to perform minimally invasive surgical procedures using an electrosurgical instrument, according to an exemplary embodiment.

This description and the accompanying drawings that illustrate exemplary embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Although for ease of description various exemplary embodiments set forth below describe electrosurgical instruments, electrosurgical units or ESU's (such as energy supply sources or energy generators), and the delivery of a flux (e.g., such as electrosurgical energy for cautery procedures, which may, for example, range from 100s of volts to 1000s of volts), those having ordinary skill in the art will appreciate that the present disclosure can be applied to a variety of surgical instruments that are provided to deliver various types of flux (e.g., other energy fluxes (such as laser, ultrasound, etc.), a fluid flux, a vacuum pressure flux, smoke evacuation, etc.) by a remotely controlled, external flux generator or other flux supply source to deliver the desired flux to a patient for use in performing, or observing, a surgical procedure. As used herein, the term "flux" may be defined as a flow useful in surgical operations that is transmitted from one unit or source to another unit or source, for example, between a flux supply unit or source and a flux delivery component, such as, for example, an electrosurgical instrument (e.g., to be delivered via end effector thereof. Therefore, it should be understood that references to electrosurgical energy generation units (ESU's) are not limited to sources of electrosurgical energy and other flux supply sources or generators are contemplated to fall within the scope of the present disclosure.

Nonlimiting examples of types of fluxes encompassed by the present disclosure, with appropriate modification to components using or transmitting the flux may include, for example, electrical energy (e.g., for cautery or nerve stimulation), laser energy, ultrasound energy, or radio frequency energy; fluids (e.g., liquids or gases); image and/or audio streams; vacuum pressure (in which case a negative pressure flux from a vacuum "source" is "delivered" to the instrument), etc. Nonlimiting examples of the flux source may include, for example, energy generators (including, for example, cautery energy and/or nerve stimulation energy generators), fluid delivery sources (e.g., for irrigation), gas supply sources, vacuum sources, etc. Further, a flux supply unit as used herein can be considered as a sink (e.g., in the case of suction).

Referring now to FIG. 1, an exemplary embodiment of a teleoperated surgical system 100A is illustrated. A nonlimiting, exemplary embodiment of a teleoperated surgical system with which the principles of the present disclosure may be utilized is a da Vinci® Si (model no. IS3000) commercialized by Intuitive Surgical, Inc. of Sunnyvale, Calif. The various exemplary embodiments described herein may also be used with the exemplary embodiments of teleoperated surgical systems described in, for example, U.S. Pub. No. US 2013/0325033, entitled "Multi-Port Surgical Robotic System Architecture" and published on Dec. 5, 2013, and U.S. Pub. No. US 2013/0325031, entitled "Redundant Axis and Degree of Freedom for Hardware-Constrained Remote Center Robotic Manipulator" and published on Dec. 5, 2013, each of which is hereby incorporated by reference in its entirety.

The teleoperated surgical system 100A is configured to perform minimally invasive teleoperated surgical procedures using instruments 101A and 101B. Instruments discussed herein may be handheld instruments or may be instruments 101A and 101B mounted on manipulator arms 120A and 120B of a patient side cart 152. Patient side cart 152 may further include an instrument 101C with a camera device or other sensor to provide a view of a surgical site. Details of various exemplary teleoperated (robotic) instruments are described in U.S. patent Nos. with publication dates and named inventor as follows: U.S. Pat. No. 6,840,938, Jan. 11, 2005, Morley et al.; U.S. Pat. No. 6,994,708, Feb. 7, 2006, Scott Manzo; U.S. Pat. No. 7,320,700, Jan. 22, 2008, Cooper et al.; U.S. Pat. No. 7,367,973, May 6, 2008, Manzo et al.; U.S. Pat. No. 8,398,634, Mar. 19, 2013, Manzo et al.; and U.S. Publication Nos. with publication dates and named inventor as follows: Ser. No. 11/238,794, Sep. 28, 2005, Scott Manzo, published as U.S. Pub. No. 2006/0079889 on Apr. 13, 2006; and Ser. No. 11/535,426, Sep. 26, 2006, Manzo et al., published as U.S. Pub. No. 2008/0046122 on Feb. 21, 2008, each of which is incorporated herein by reference in its entirety.

Each of the instruments 101A and 101B may be manipulated as a slave manipulator and remotely controlled by control signals received from a surgeon's console 150. In contrast, manual endoscopic surgical instruments are directly controlled by hand. For instance, a control cable 110 may couple a computer 151B of a control cart 150B and the surgeon's console 150 to control the surgical system. Control cart 150B may further include an assistant's display 154 to facilitate viewing of an internal surgical site. Patient side cart 152, surgeon's console 150, and control cart 150B may be configured according to the exemplary embodiments of U.S. Pub. No. US 2013/0325033, entitled "Multi-Port Surgical Robotic System Architecture" and published on Dec. 5, 2013, and U.S. Pub. No. US 2013/0325031, entitled "Redundant Axis and Degree of Freedom for Hardware-Constrained Remote Center Robotic Manipulator" and published on Dec. 5, 2013, each of which is hereby incorporated by reference in its entirety.

Surgical instruments may be non-electrosurgical instruments or electrosurgical instruments. Generally, electrosurgical instruments and systems can be used for electrosurgical treatment of tissue during minimally invasive surgical procedures. For example, electrosurgical instruments may be capable of treating tissue with heat produced by electrical energy while cutting, shearing, grasping, engaging, or contacting treatment tissue. To support the functionality of electrosurgical instruments, teleoperated surgical system 100 may further include one or more ESU's 102A-102B. ESU's of the exemplary embodiments herein may have settings and functions according to the exemplary embodiments of U.S. Pat. No. 8,423,182, published on Apr. 16, 2013, which is hereby incorporated by reference herein in its entirety. The one or more ESU's 102A-102B may be remotely controlled by a surgeon via surgeon's console 150.

According to an exemplary embodiment, one or more flux transmission conduits may couple an electrosurgical instrument to an ESU so that a flux may be supplied from an ESU to support and enable the functionality of the electrosurgical instrument. For instance, cables 106A, 106B, 107 may couple electrosurgical instruments 101A, 101B to ESU's, as shown in the embodiment of FIG. 1. Instruments 101A, 101B may be connected to the same ESU or to different ESU's. According to an embodiment, instrument 101A may be a bipolar electrosurgical instrument that is connected to an ESU via a pair of wires 106A, 106B. According to an exemplary embodiment, instrument 101B may be a monopolar electrosurgical instrument connected to an ESU via a wire 107.

According to an exemplary embodiment, a ground wire 108 may be provided to couple a monopolar ESU 102B and patient (not shown). For instance, patient may be coupled to the monopolar ESU 102B via a grounding electrode 113 in contact with the body of the patient. The grounding electrode 113 may be in the form of a pad, for example, having at least one electrically conductive surface that is connected to the ground wire 108. The pad may be in the form of a single surface or the pad may be split to provide dual contact surfaces, although a greater number of contact surfaces may be used. An example of a grounding pad is the NESSY® neutral electrode safety system, which is manufactured by ERBE USA, Inc. of Marietta, Ga.

An electrosurgical unit itself may include controls to facilitate use of the electrosurgical unit. For instance, although the electrosurgical units 102A'-102N' may be actuated remotely, such as via a surgeon's console 150A, settings for the electrosurgical units 102A'-102N' may be controlled directly by interfacing with the controls of the electrosurgical units 102A'-102N' themselves. Such controls may be useful, for example, during pre-operative setup when the settings for an electrosurgical unit are being selected according to a desired use for the electrosurgical unit and/or according to an electrosurgical instrument that is provided a flux by the electrosurgical unit. However, the controls of conventional ESU's have been somewhat complex, hierarchical, and not particularly informative.

Therefore, various exemplary embodiments of ESU's described herein have a user control interface that is simple to use, yet informative of the various settings for the ESU. Such an ESU may advantageously reduce the amount of setup time for a surgical procedure, permit quick and correct connections between an ESU and electrosurgical instruments, and allow faster changes to ESU settings with little or no training for personnel.

Figure 2:
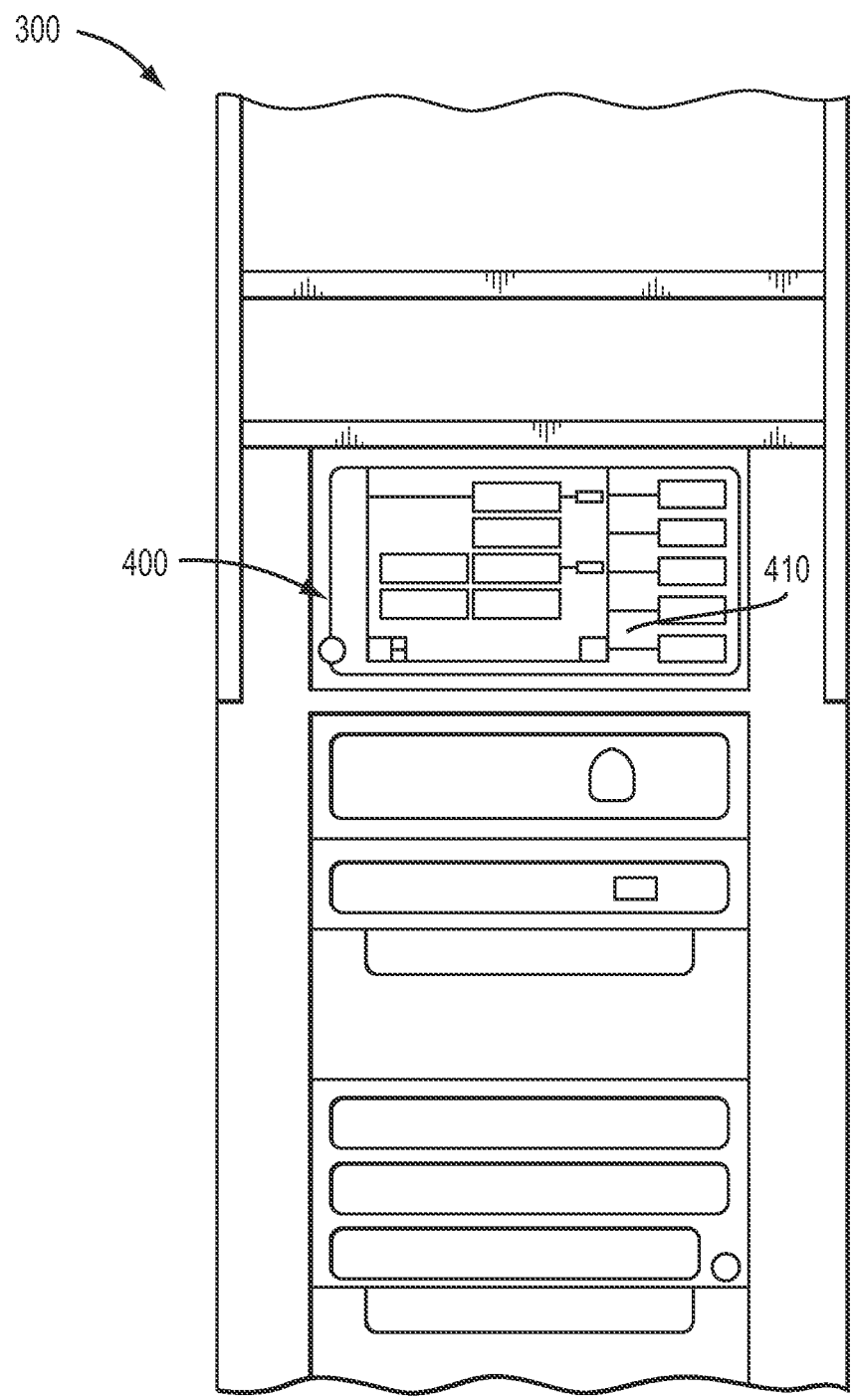
FIG. 2 is a front view of an exemplary embodiment of a control cart that includes an ESU.

Turning to FIG. 2, a partial view of an exemplary embodiment of a control cart 300 is shown that includes an ESU 400 having a user control interface 410. The control cart 300 may be arranged as described in the exemplary embodiment of FIG. 1. ESU 400 may be used with an electrosurgical instrument, such as an electrosurgical instrument configured to be mounted to a teleoperated surgical system, or a non-teleoperated electrosurgical instrument, such as a hand-held instrument. Further, ESU 400 may be used to actuate electrosurgical instruments that are mounted to a teleoperated surgical system or to actuate electrosurgical instruments not mounted to a teleoperated surgical system, such as to test functionality of an instrument during setup.

Figure 3:
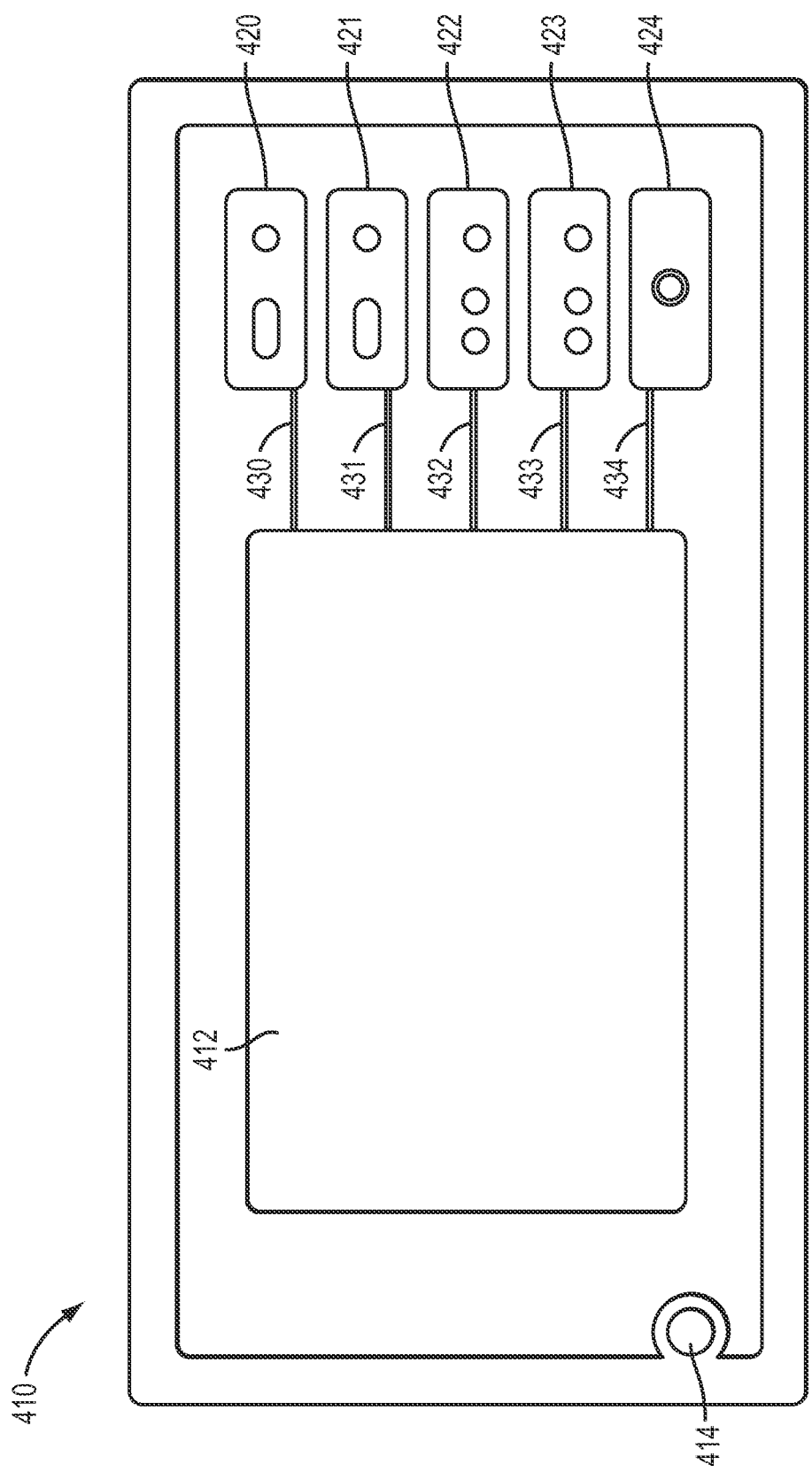
FIG. 3 is a front view of an exemplary embodiment of a user control interface of an ESU.

As shown in the exemplary embodiment of FIG. 3, the user control interface 410 of the ESU 400 may include a display 412, a power switch 414, and one or more instrument connectors or ports 420-424 (referred to as "connectors" below) configured to supply a flux to an instrument. Although the exemplary embodiment of FIG. 3 shows five connectors 420-424, ESU 400 may include other numbers of connectors. For example, an ESU may include one, two, three, four, five, or more connectors. Display 412 may provide a graphical user interface for a user to control and change settings for the ESU 400. According to an exemplary embodiment, display 412 may be a touchscreen that a user may press to actuate controls and settings displayed on the touchscreen. A touchscreen may be actuated by, for example, being pressed by a finger of a user or other object (e.g., stylus) capable of applying a pressure to a particular area of the touchscreen.

Connectors 420-424 may, for example, provide connections between the ESU 400 and one or more electrosurgical instruments via, for example, flux transmission conduits. Transmission of the flux from a flux source, such as the ESU 400, to a surgical instrument can be via a flux transmission conduit, such as, for example, an electrical energy transmission cable, a hose, a fiber optic cable, etc., configured to be connected to the surgical instrument at one end and to a flux source. As will be discussed below, connectors 420-424 may be configured to connect via flux transmission conduits with different types of electrosurgical instruments, such as, for example, monopolar or bipolar electrosurgical instruments. Further, one or more connectors 420-424 may be configured to connect an electrode, such as a neutral ground electrode for a monopolar instrument.

According to an exemplary embodiment, connectors 420-424 may be configured so that a connection for an electrosurgical instrument may only be inserted in a desired, predetermined orientation. To assist a user with connecting an electrosurgical instrument according to a desired, predetermined orientation, a connector may include one or more orientation indicators. For instance, as shown in FIG. 5, a connector 424 may include a visual orientation indicator 425 that may be aligned with an orientation indicator 426 of a connector 427 of a flux transmission conduit for an electrosurgical instrument to assist with proper orientation of the connector 427 with the connector 424.

The user control interface 410 includes both physical components, such as connectors 420-424, and information provided on display 412 related to electrosurgical instruments connected via connectors 420-424. To assist a user with determining which information and controls of an ESU are associated with a particular electrosurgical instrument, the display 412 may be partitioned into different display screen sections that correspond, such as, for example, in a visual arrangement, to different electrosurgical instruments. The partitioned sections of the display 412 may be distinct from one another so that a user may easily determine the particular area of the display 412 that provides information about the settings for a particular electrosurgical instrument and the controls for that instrument. Further, the user control interface 410 may be arranged in a manner that is aesthetically appealing and informative to a user. Sections of display 412 may be partitioned from one another by, for example, providing space between the display screen sections, providing separate borders around the display screen sections, providing sections with different shapes and/or sizes, making different sections different colors, and other means of delineating different areas recognized by those having ordinary skill in the art.

According to an exemplary embodiment, all controls and/or settings information for each connector may be advantageously displayed at once on display 412 via the partitioned display screen sections so that a user may easily associate and access the information and controls with a particular instrument, while minimizing or eliminating the need to cycle through different menus or pages on the display that each provide information and/or controls for the different electrosurgical instruments.

Figure 4:
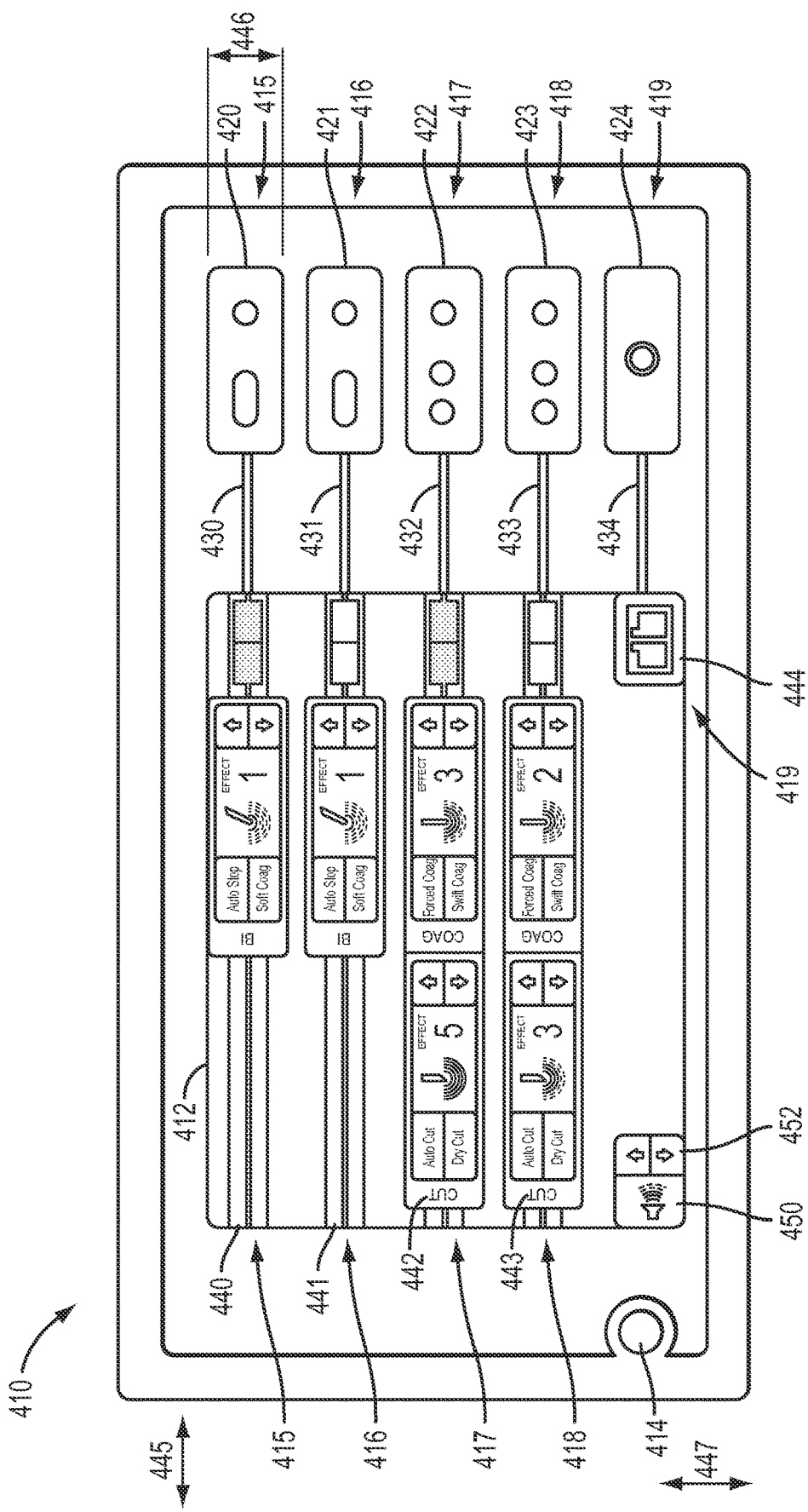
FIG. 4 is a front view of an exemplary embodiment of a user control interface and display of an ESU.

As shown in the exemplary embodiment of FIG. 4, display 412 may be partitioned into display screen sections 440-444 associated with connectors 420-424. Although the exemplary embodiment of FIG. 4 shows display 412 partitioned into five display screen sections 440-444, the number of display screen sections is not limited to this number. For instance, the number of display screen sections may equal the number of connectors 420-424. The number of display screen sections may be, for example, one, two, three, four, five, or more display screen sections. Further, although the exemplary embodiment of FIG. 4 shows an ESU arrangement in which display screen sections and connectors are arranged horizontally, the arrangement of ESU is not limited to a horizontal arrangement, as will be discussed below. For instance, connectors and display screen sections may be arranged vertically above and below one another. In another instance, connectors and display screen sections may be arranged radially, with display screen sections arranged centrally relative to connectors arranged radially from the display screen sections, or vice versa.

Display 412 may be a single, continuous screen including a plurality of display screen sections 440-443 on a single display (e.g., without needing to cycle through various windows or display tabs). For example, the information and/or controls of display screen sections 440-443 may displayed at the same time so that a user need not switch windows or display tabs to view the information and/or controls for different surgical instruments operatively coupled to connectors of interface 410. As will be discussed below, the various display screen sections 440-443 may display information and/or controls for different types of surgical instruments (e.g., monopolar and bipolar electrosurgical instruments). Thus, a user of user control interface 410 may easily view information and/or controls related to various surgical instruments without needing to switch to a different window on a screen or to look at a separate screen.

Each display screen section 440-444 may provide information (e.g., instrument type, settings of instrument, settings of ESU, connection state, etc.) pertaining to the respective electrosurgical instrument connected to one of connectors 420-242 that the display screen section is associated with. For instance, display screen section 440 may be associated with connector 420, display screen section 441 may be associated with connector 421, display screen section 442 may be associated with connector 422, display screen section 443 may be associated with connector 423, and display screen section 444 may be associated with connector 424 so that each display screen section provides a variety of information for an electrosurgical instrument connected to the associated connector. Information provided by display screen sections may include, for example, interfaces for control of settings. Other arrangements are also contemplated as being in the scope of the present disclosure and claims, with variations being apparent to those having ordinary skill in the art from the present disclosure.

To assist a user with associating connectors with displayed information, the sections of display 412 may be visually coupled with the connectors of the user control interface 410. In other words, user control interface 410 may provide mode and/or effect controls on a per-energy module basis, with each energy module including at least one display screen section and at least one connector that are respectively associated with one another. For instance, display screen sections 440-444 of display 412 may be physically arranged relative to connectors 420-424 so that available controls to adjust settings for a given connector are located along a common direction. Further, by visually coupling display screen sections and connectors according the exemplary embodiments described herein, a user may easily identify and/or remember which display screen sections are respectively associated with which connectors.

According to an exemplary embodiment, display screen sections 440-444 may be located within display 412 so that display screen sections 440-444 are visually coupled with connectors 420-424. As shown in the exemplary embodiment of FIG. 4, one manner by which to visually couple display screen sections 440-444 with connectors 420-424 is to horizontally align the display screen sections 440-444 and the connectors 420-424. This may result in visually coupled connectors 420-424 and display screen sections 440-444 being arranged in pairs. For instance, each horizontal pair may include one display screen section and one associate connector, with different pairs of connectors and display screen sections being vertically arranged above and below one another, as shown in the exemplary embodiment of FIG. 4. As a result, in the exemplary arrangement of FIG. 4, a user need only look laterally in a horizontal direction from a particular display screen section to find the connector that is coupled with the display screen section, or vice versa, with minimal or no training. In another example, if display screen sections and connectors are arranged vertically above and below one another, a user need only look vertically upwards or downwards in a vertical direction to find display screen sections and connectors coupled with one another.

One manner of visually coupling display screen sections 440-444 with connectors 420-424 is to arrange connectors 420-424 and display screen sections 440-444 in a series of vertically spaced rows. For instance, a display screen section 440 and its associated connector 420 may be located on user control interface 410 at a same height or vertical position with respect to a vertical direction 447, as shown in FIG. 5. Thus, a user need only to visually scan a user control interface 410 laterally along a row to determine which display screen sections 440 and connectors 420-424 are coupled with one another. According to another exemplary embodiment, vertically arranged connectors and display screen sections may be arranged in columns so that a user may easily determine coupled connectors and display screen sections within a given column.

According to an exemplary embodiment, connectors 420-424 may be positioned along a long axis of their respective associated display screen sections 440-444. For instance, display screen section 440 may have a long axis 445 directed toward connector 420, which is coupled with display screen section 420. Thus, as a user laterally scans the information displayed by display screen section 440, the user may continue to laterally scan in a horizontal direction along long axis 445 across the user control interface 410 to find the connector 420 coupled with display screen section 440.

Another manner of visually coupling display screen sections 440-444 with connectors 420-424 is to provide display screen sections with a predetermined shape, according to an embodiment. As shown in the exemplary embodiment of FIG. 4, display screen sections 440-444 may have a rectangular or bar shape. Such a shape may be advantageously used to visually couple a given display screen section with an associated connector. Display screen section 440 may be in the shape of a bar or rectangle so that the shape of the display screen section 440 guides a user's gaze toward the associated connector 420 by visually orienting the shape of display screen section 440 toward connector 420. For instance, as a user laterally scans the information displayed within the predetermined shape of display screen section 440, the user may be directed along the length of the predetermined shape to associated connector 420. In another instance, the predetermined shape of display screen section 440 may have a long axis 445 that associated connector 420 is positioned along, as discussed above. According to an exemplary embodiment, at least some of the information provided by a display screen section may be contained within the shape of the bar or rectangle so that a user may easily identify what information is coupled with a particular display screen section.

Another method of visually coupling display screen sections 440-444 with connectors 420-424 is to provide display screen sections with a predetermined dimension that is substantially the same as a corresponding predetermined dimension of their respective associated connectors 420-424, according to an exemplary embodiment. The predetermined dimension, for example, may be aligned substantially perpendicular to a direction along which display screen sections and connectors are visually coupled. According to an exemplary embodiment, when display screen sections and connectors are visually coupled along a horizontal direction the predetermined dimension can be the vertical height of the display screen sections and the connectors. For instance, display screen section 440 and associated connector 420 may each have a vertical height 446 that is substantially the same, as shown in the exemplary embodiment of FIG. 4, so that a user may visually associate a display screen section with a connector in a relatively easy manner. According to another embodiment, the predetermined dimension can be a horizontal width when display screen sections and connectors are visually coupled along a vertical direction. For instance, associated display screen sections 440-444 and connectors 420-424 may have substantially the same vertical height and may have substantially the same vertical position on a user control interface 410 and/or be both positioned along a long axis of the display screen section, as discussed above.

According to an exemplary embodiment, display screen sections 440-444 and connectors 420-424 may be visually coupled via the use of color. For instance, when display screen section 440, or a portion thereof, and connector 420 may have the same color so that a user may easily identify that display screen section 440 and connector 420 are visually coupled and respectively associated with one another due to their common color. For example, border 428 of connector 424 in the exemplary embodiment of FIG. 5 may have the same color as a display screen section 440, or portion thereof. Further, connector 427 may have the same color as border 428 and display screen section 440, or portion thereof, to assist a user with associating connector 427, connector 424, and display screen section 440, or portion of display screen section 440. The color may be provided, for example, by a border around each of a display screen section and a connector, or a background color may be used for each display screen section and connector that are respectively associated with one another. Further, different colors may be used for different couplings of display screen sections and connectors. For instance, a first color may be used to respectively associate display screen section 440 and connector 420, a second color may be used to respectively associate display screen section 441 and connector 421, a third color may be used to respectively associate display screen section 442 and connector 422, and so on. According to an exemplary embodiment, a color may be selected to identify a type of instrument or operation associated with a respective display screen section and connector. For instance, color may be respectively selected to identify a respective display screen section, or portion thereof, and connector as being for monopolar, bipolar, or grounding operations and instruments.

According to an exemplary embodiment, any of the techniques of visually coupling display screen sections 440-444 with connectors 420-424 may be used alone or together, for example, in a combination of two or more techniques. Further, although the embodiment of FIG. 4 shows display screen sections 440-444 and connectors 420-424 aligned horizontally, display screen sections 440-444 and connectors 420-424 may be arranged in other directions. For instance, with reference to the exemplary embodiment of FIG. 23, a user control interface 810 may be configured so that display screen sections 840-844 of a display 812 and connectors 820-824 are arranged vertically as modules 815-819, which will be discussed below. Modules 815-819 include pairs of display screen sections 840-844 and connectors 820-824 arranged side-by-side in a lateral, horizontal direction, as shown in the exemplary embodiment of FIG. 23. Display screen sections and their corresponding connector may have substantially the same horizontal width and may be positioned in substantially the same horizontal position on interface 810. For instance, display screen section 840 and connector 820 may have substantially the same horizontal width 846. Modules 815-819 may further include visual indicators 830-834, which will be discussed further below.

Figure 23:
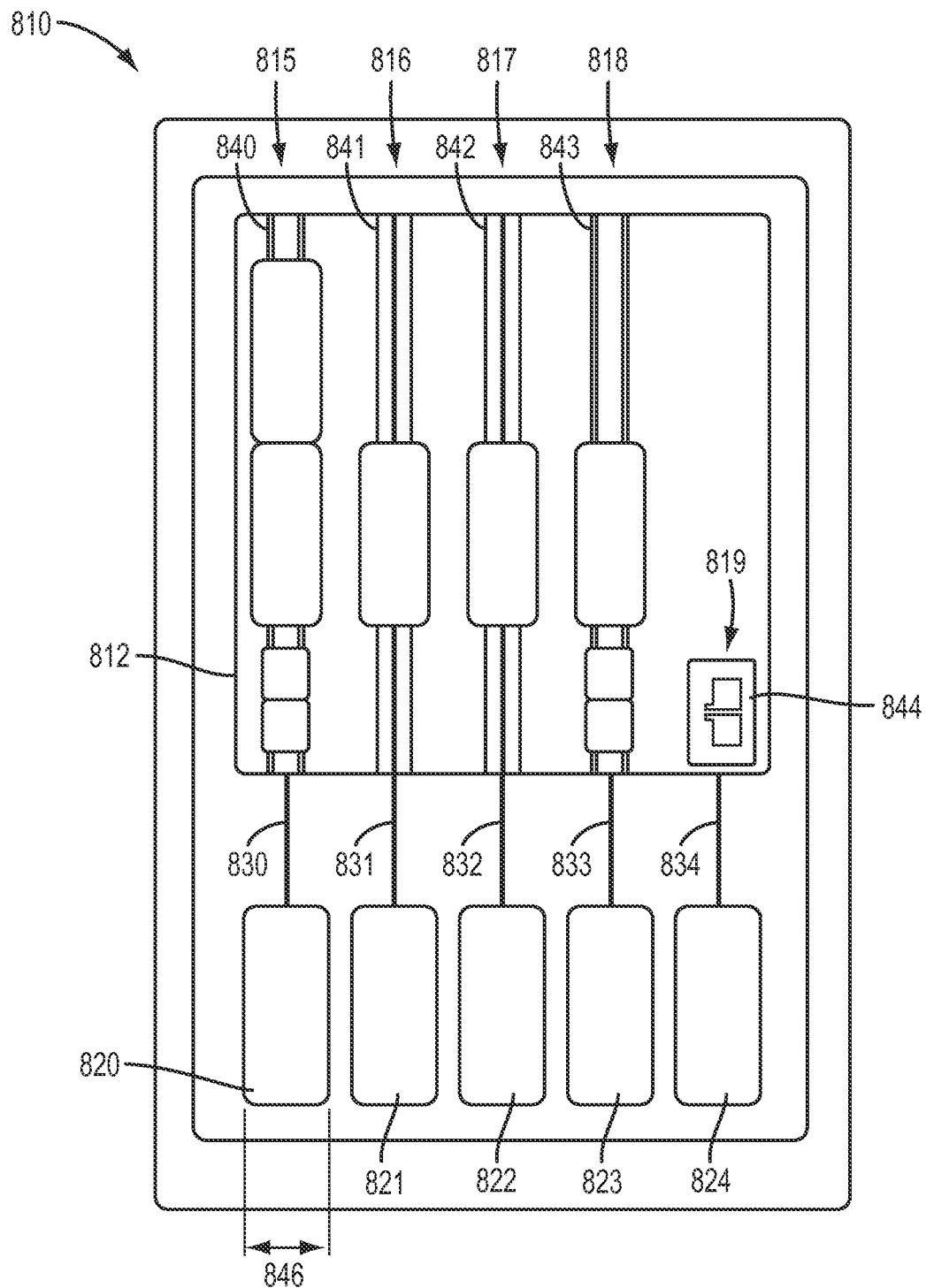
FIG. 23 is a front view of an exemplary embodiment of a user control interface and display of an ESU in which display screen sections and connectors are visually coupled in a vertical direction.
Figure 24:
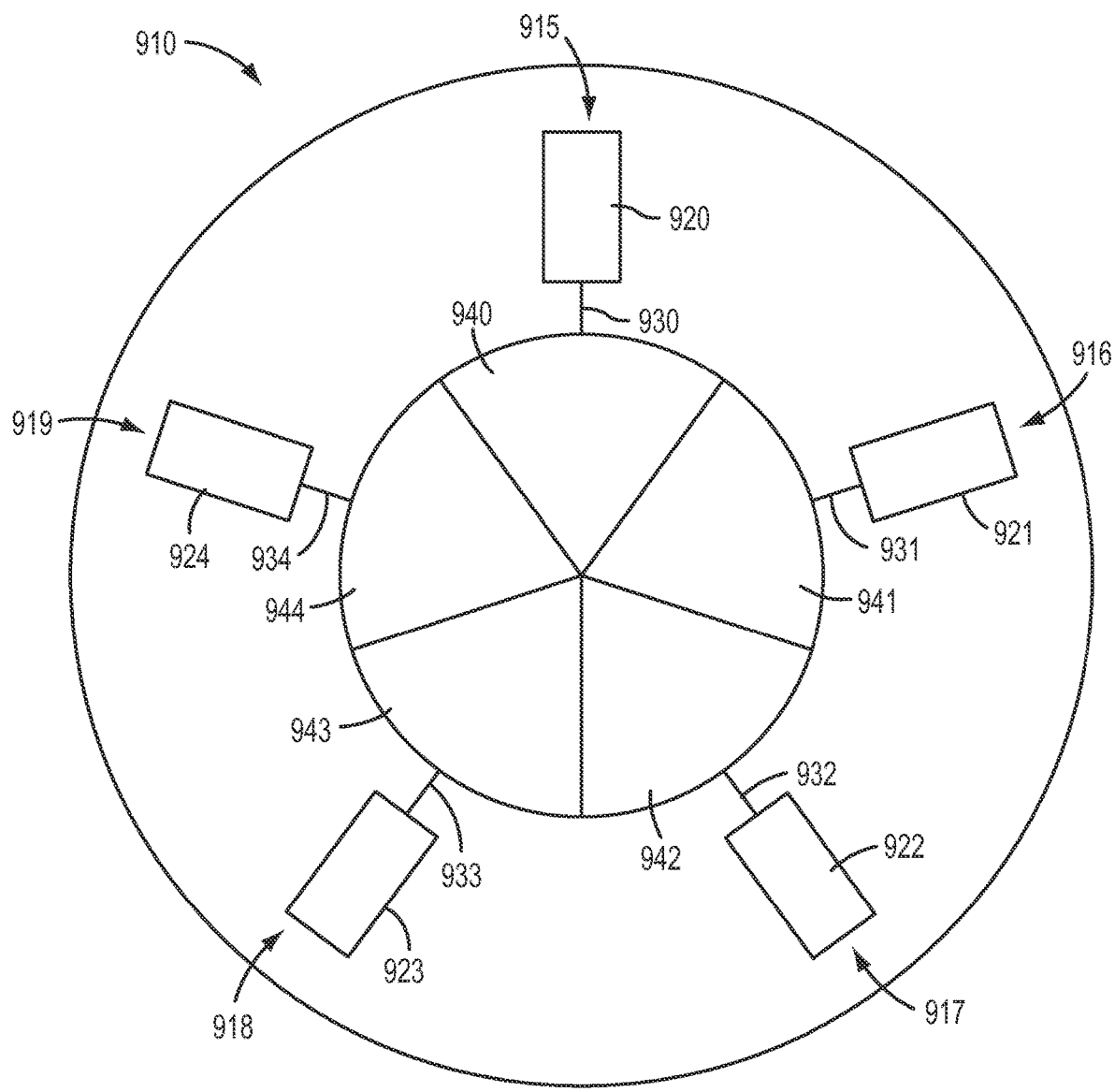
FIG. 24 is a front view of an exemplary embodiment of a user control interface and display of an ESU in which display screen sections and connectors are visually coupled in a radial manner.

Although the exemplary embodiments of FIGS. 4 and 23 provide user control interfaces and display screen sections in a relatively linear manner in Cartesian coordinates, other shapes and arrangements may be selected to visually couple display screen sections and connectors to assist a user with associating a respective display screen section with its connector or connectors. As shown in the exemplary embodiment of FIG. 24, a user control interface 910 may be arranged to have a radial configuration. For instance, a display 912 may be partitioned into display screen sections 940-944 in a center of interface 910, with connectors 920-924 located radially outward from display screen sections 940-944 to define modules 915-919 that include display screen sections 940-944 and connectors 920-924. Modules 915-919 may further include visual indicators 930-934, which will be discussed below. According to another exemplary embodiment, user control interface 910 may be configured so that connectors 920-924 are arranged in a center of the interface 910 and display screen sections 940-944 are located radially outward from connectors 920-924.

As discussed above, user control interface 410 includes both physical structures, such as connectors 420-424, and information in the partitions of display 412, such as via display screen sections 440-444. To further assist a viewer to associate display partitions with the physical structures, the user control interface 410 may include one or more visual indicators. As shown in the exemplary embodiment of FIGS. 3 and 4, user control interface 410 may include visual indicators 430-434 to provide a visual link between visually coupled display screen sections 440-444 and connectors 420-424. For instance, visual indicators 430-434 may be respectively located between display screen sections 440-444 and connectors 420-424. Thus, visual indicator 430 may further visually couple display screen section 440 with connector 420, visual indicator 431 may further visually couple display screen section 441 with connector 421, visual indicator 432 may further visually couple display screen section 442 with connector 422, visual indicator 433 may further visually couple display screen section 443 with connector 423, and visual indicator 434 may further visually couple display screen section 444 with connector 424. Visual indicators may be visually coupled with display screen sections and connectors according to the exemplary embodiments described above. For instance, visual indicators, connectors, and display screen sections may be aligned (e.g., such as horizontally, vertically, in a hub-and-spoke alignment, diagonally, etc.) with one another; visual indicators and connectors may be positioned along substantially the same axis (e.g., a long axis of a display screen section); visual indicators, connectors, and display screen sections may substantially have a same relative horizontal or vertical dimension; visual indicators, connectors, and display screen sections may be positioned at substantially the same vertical position; and/or a display screen section may have a shape of a bar and a visual indicator and a connector may be positioned along a long axis of the bar.

Visual indicators 430-434 may be physically provided on the face of the user control interface 410. For instance, visual indicators 430-434 may be, for example, lines painted or otherwise drawn upon the face of the user control interface 410. In another example, visual indicators 430-434 may be grooves or indentations formed in the face of interface 410 and extending between the display 412 and connectors 420-424.

According to an exemplary embodiment, visual indicators 430-434 may have a shape to assist with the function of visually coupling display screen sections 440-444 with connectors 420-424. For instance, visual indicators 430-434 may be in the shape of lines or bars that extend between associated display screen sections and connectors, as shown in the exemplary embodiment of FIG. 4. Further, the shape of visual indicators 430-434 may be selected so that the visual indicators 430-434 are aligned along a direction that visually couples display partitions with connectors. As shown in the exemplary embodiment of FIG. 4, visual indicators 430-434 may be in the shape of lines, bars, or other graphics that extend substantially along the same direction as a long axis 445 of display screen sections 440-444. Therefore, the alignment of visual indicators 430-434 may direct a user's gaze towards an associated connector 420-424 when the user is scanning the information and controls of display screen sections 440-444, whether scanning is in a lateral (horizontal) direction, a vertical direction, a radial direction, or other direction.

According to an exemplary embodiment, a user control interface 410 need not include visual indicators 430-434. For instance, a user control interface 410 may be arranged so that display partitions and connectors 420-424 are arranged immediately adjacent to one another. For instance, connectors 420-424 and display partitions may be arranged so that a user scanning along a display screen section 440-444 observes a connector 420-424 when the user's gaze leaves the area of the display 412, whether the direction of scanning is a lateral direction, a vertical direction, or a radial direction. According to an exemplary embodiment, no display screen section, connector, control, or other feature is located between the display screen sections 440-444 and the connectors 420-424 to reduce any confusion about which display screen section is aligned or otherwise associated with a particular connector.

By arranging the display 412 into partitions visually coupled with connectors 420-424, the user control interface 410 may be arranged into modules. Each module may include, for example, a display partition and a connector associated together for the control of a particular electrosurgical instrument. In other words, a module may include one or more display screen sections and one or more connectors. According to an exemplary embodiment, a module may include a single display screen section and a single connector as a pair, although the exemplary embodiments described herein are not limited to this configuration and a module may include, for example two more connectors or two more display screen sections (i.e., modules are not limited to a one-to-one correspondence between display screen sections and connectors but may instead include a single display screen section and a plurality of connectors or a single connector and a plurality of display screen sections, among other configurations). For instance, display screen section 440 and connector 420 may provide a first module 415 for a first electrosurgical instrument, display screen section 441 and connector 421 may provide a second module 416 for a second electrosurgical instrument, display screen section 442 and connector 422 may provide a third module 417 for a third electrosurgical instrument, display screen section 443 and connector 423 may provide a fourth module 418 for a fourth electrosurgical instrument, and display screen section 444 and connector 424 may provide a fifth module 419. Thus, a module 415-419 may allow a user to easily find and use controls and settings information for a particular electrosurgical instrument that is connected to one of connectors 420-424 and associated with one of display screen sections 440-444 to provide an overall module dedicated to the electrosurgical instrument connected to the respective connector of the module.

Turning to FIG. 6, an exemplary embodiment of a module 460 is shown. Module 460 may include display screen sections 470 and 472 and connector 464. According to an exemplary embodiment, module 460 may further include a visual indicator 466. Display screen sections 470 and 472, connector 464, and visual indicator 466 may be configured according to the embodiments described above.

According to an exemplary embodiment, a display screen section of a module may include one or more mode display portions that provide information about an electrosurgical instrument associated with the display screen section. Thus, according to an exemplary embodiment, a display 412 of a user control interface 410 may include one or more display screen sections 440-444 and the display screen sections 440-444 may be further divided into display portions. According to an exemplary embodiment, a display portion may include control(s) for and/or information about an operational mode of an electrosurgical instrument. Modules 415, 416 that include display screen sections 440, 441 and connectors 420, 421 in FIG. 5 are exemplary embodiments of bipolar modules.

An electrosurgical instrument may be configured to operate in more than one mode and the number of mode display portions for a particular display screen section may depend upon, for example, the type of energy or flux supplied to an electrosurgical instrument by a given module. For instance, a monopolar module may have two mode display portions. As shown in the exemplary embodiment of FIG. 6, a monopolar module 460 may include a first mode display portion 470, such as for a cut function, and a second mode display portion 472, such as for a coagulation. The modules 417, 418 provided by mode display portions 442, 443 and connectors 422, 423 in the exemplary embodiment of FIG. 4 also provide examples of monopolar modules. As shown in the exemplary embodiment of FIG. 4, a module 419, which will be discussed below, may also be provided for a ground electrode. In contrast, a bipolar module may include only a single display portion, such as display portions 440 and 441 in the exemplary embodiment of FIG. 4. According to an exemplary embodiment, adjustments to settings via a mode display portion and cessation of providing flux to an instrument by using a display portion are not permitted while the ESU is activated to provide a flux to the instrument.

A mode display portion of a module may include settings information and/or controls for the mode represented by the mode display portion. As shown in FIG. 6, a mode display portion 470 may include a mode identification 471 to identify which mode is represented by mode display portion 470 and being utilized by an electrosurgical instrument connected to module 460 via connector 464. The mode identification 471 may be, for example, text located in a border of the mode display portion 470 naming the mode being utilized. In another example, a mode may be identified by methods other than text or symbols. For instance, a mode may be identified by a color, such as a colored border for display portions 470 and 472, to represent the mode. According to an exemplary embodiment, a mode display portion 470 representing a cut mode of a monopolar module 460 may have, for example, a yellow border, while a mode display portion 472 of a monopolar module 460 representing a coagulation mode may have, for example, a blue border. The various colors used may be those commonly used as standards, depending on, for example, a particular application utilized. Other colors may be selected to indicate the various modes and other visual indicators may be used to identify mode. According to an exemplary embodiment, different visual patterns may be used to indicate different modes. According to an exemplary embodiment, mode identifications 471 may include a plurality of mode identifiers, such as a combination of text, symbols, color, and/or other identifications of a mode.

Although a display screen section may be associated with only one operational state (i.e., mode), a display screen section may be associated with more than one operational state that may be selected by a user. If an electrosurgical instrument may operate in different states (i.e., modes), the mode display portion 470, 472 may further include one or more mode switches 473 to permit selection of a mode state. According to an exemplary embodiment, a mode switch 473 may include identification of the different operational states available for a particular mode and which state is selected, including a color identifying a mode state. Various modes that may be used with an ESU are described in the VIO 300 D User Manual, 2009, from ERBE GmBH of Germany, which is hereby incorporated by reference in its entirety.

Mode display portions 470, 471 may include further controls and/or displays of information for various parameters of an operational state (i.e., mode) represented by a display portion 470, 471. According to an exemplary embodiment, a mode display portion 470, 472 may include an intensity control 479 to control the amount or intensity of flux provided by module 460 for an operational state (for those modes that may be adjusted in intensity. Mode display portions 470, 471 may further include an intensity indicator 477 to display the intensity selected by an intensity control 479. In addition, a mode display portion 470, 472 may include an effect icon 475 to easily permit a user to identify an operational state (i.e., mode). Further, effect icon 475 may visually indicate an intensity selected by intensity control 479, such as by graphically displaying the selected intensity.

Although the features of the exemplary embodiment of FIG. 6 have been discussed with regard to a monopolar module 460 including two display portions 470, 472, the features of the exemplary embodiment of FIG. 6 may be applied to a bipolar module including a single display portion, such as modules 440 and 441 in the exemplary embodiment of FIG. 4.

According to an exemplary embodiment, display screen sections 470 and 472, connector 464, and visual indicator 466 may be arranged along a long axis of module 460, which may be coincident with a smart electrosurgical instrument indicator 480 (discussed below). Further settings and/or information within display screen sections 470 and 472 may be arranged along the long axis of module 460. For instance, mode identification 471, mode switches 473, effect icon 475, intensity indicator 477, and intensity control 479 of mode display portions 470 and 472 may all be arranged along the long axis of module 460. For example, a long axis of module 460 (i.e., a substantially straight line) may pass through each of mode identification 471, mode switches 473, effect icon 475, intensity indicator 477, and intensity control 479 of mode display portions 470 and 472.

According to an exemplary embodiment, a module may include an indicator that an electrosurgical instrument associated with the module is being activated and used. For instance, when an electrosurgical instrument (not shown) associated with module 460 is activated, module 460 may display an indication that an operational state (i.e., mode) has been activated. For instance, a border of a mode display portion 470 or 472 of module 460 may light up, flash, and/or change color to indicate that the coagulation mode is being used for an electrosurgical instrument connected to module 460. In another embodiment, mode display portions 470, 472 may light up, change color, flash and/or provide another visual indication that the associated mode is being used.

Some electrosurgical instruments may be "smart" instruments that can provide information about the electrosurgical instrument. For instance, an electrosurgical instrument may include a device that stores information about the electrosurgical instrument. The device may be, for example, a printed circuit board, flash memory, EEPROM, or other type of non-volatile memory. The information may include, for example, instrument type information to identify the type of electrosurgical instrument that is coupled to a manipulator arm, what type of electrosurgical energy the instrument is configured to receive (e.g., bipolar or monopolar cutting & monopolar coagulating), and/or other information useful for an electrosurgical instrument. This identification information may be received and utilized to determine compatibility for the instrument so that the electrosurgical instrument may be properly controlled by the master control console.

According to an exemplary embodiment, a module for an electrosurgical instrument may include an indicator for when a smart instrument is connected to the module. The indicator may be in the form of, for example, a lightened area, a symbol, color, or other visual indication to easily inform a user that a connected instrument is a smart instrument. As shown in the exemplary embodiment of FIG. 6, module 460 may include a smart electrosurgical instrument indicator 480 that lightens or turns color when a connected electrosurgical instrument is a smart electrosurgical instrument.

According to an exemplary embodiment, a smart electrosurgical instrument indicator 480 may have a shape that enhances association of display screen sections with connectors. For instance, a smart electrosurgical instrument indicator 480 may be in the form of a line or bar that laterally extends across a display screen section 462 of a module 460 towards a connector 464 associated with the display screen section 462, as shown in the exemplary embodiment of FIG. 6. Thus, when smart electrosurgical instrument indicator 480 lights up or changes color to indicate connection to a smart electrosurgical instrument, indicator 480 may also assist a user with associating display screen section 462 with connector 464. In addition, when module 460 includes a visual indicator 466, as shown in the exemplary embodiment of FIG. 6, smart electrosurgical instrument indicator 480 may be aligned with or substantially coaxial with visual indicator 466 to assist with association of display screen section 462 with connector 464.

When a smart electrosurgical instrument is not connected to a module, such as via connector 464 for module 460 in the exemplary embodiment of FIG. 6, smart electrosurgical instrument indicator 480 may be inactive. For instance, smart electrosurgical instrument indicator 480 may appear dark when no instrument is connected to a module or when an instrument is connected but the instrument is not a smart instrument.

According to an exemplary embodiment, smart electrosurgical instrument 480 indicator may form a background or border within a teleoperated system indicator 482 (discussed below) and/or foot pedal assignment indicator 484 (discussed below) so that when smart electrosurgical instrument indicator 480 is activated, the background or border for teleoperated system indicator 482 and/or foot pedal assignment indicator 484 are activated as well.

Electrosurgical instruments connected to modules of an ESU may be connected to a teleoperated surgical system or may be handheld instruments. For instance, an electrosurgical instrument may be connected to a manipulator arm of a teleoperated surgical system, as discussed in the embodiments of FIG. 1 above. Modules may include an indicator that an electrosurgical instrument is mounted or otherwise connected to a teleoperated surgical system so a user may easily understand which instrument is associated with a module. For instance, an ESU may sense or receive a signal that an electrosurgical instrument has been mounted to a teleoperated surgical system and then provide an indication to a user that the electrosurgical instrument is installed to the teleoperated surgical system.

Figure 7:
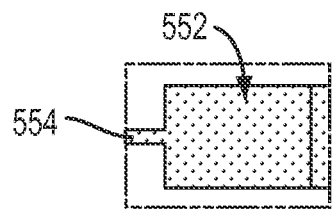
FIG. 7 is a front view of a system installation indicator in a deactivated state, according to an exemplary embodiment.
Figure 8:
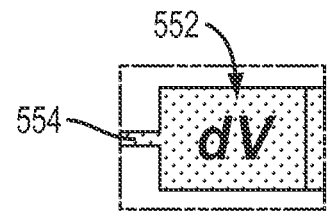
FIG. 8 is a front view of a system installation indicator in an activated state, according to an exemplary embodiment.
Figure 15:
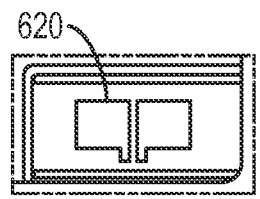
FIG. 15 is a front view of a display screen section for a ground electrode indicating no connection with a ground electrode having two contact surfaces, according to an exemplary embodiment.

As shown in the exemplary embodiment of FIG. 6, a module 460 may include a system installation indicator 552. FIG. 6 shows a system installation indicator 552 in a deactivated state, which informs a user that an instrument associated with module 460 is not installed on a teleoperated surgical system. FIGS. 7 and 8 show an exemplary embodiment of a system installation indicator 552, with system installation indicator 552 shown in a deactivated state in FIG. 7 (no indicator is shown) and in an activated state in FIG. 8. As shown in the exemplary embodiment of FIGS. 7 and 8, system installation indicator 552 may be connected to or located within a smart electrosurgical instrument indicator 554. As discussed above, smart electrosurgical instrument indicator 554 may form a border of the system installation indicator 552 or form a bar or rectangle that the system installation indicator 552 is located within. In both of FIGS. 7 and 8 the smart electrosurgical instrument indicator 554 is activated, causing the background of system installation indicator 552 to be activated. FIG. 15 depicts both the smart electrosurgical instrument indicator 554 and the system installation indicator 552 in an activated state.

Figure 9:
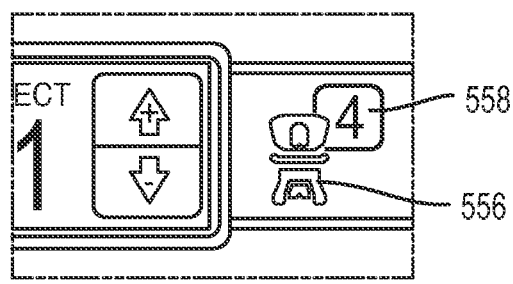
FIG. 9 is a front view of a system installation indicator including a second indicator, according to an exemplary embodiment.
Figure 10:
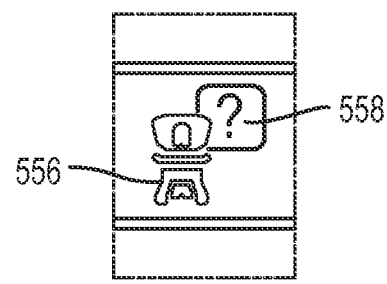
FIG. 10 is a front view of a system installation indicator including a second indicator indicating an error, according to an exemplary embodiment.

Aside from indicating that an electrosurgical instrument is mounted to a teleoperated surgical system, a system installation indicator may provide additional information to a user. Turning to FIG. 9, an exemplary embodiment of a system installation indicator 556 is shown that indicates whether an electrosurgical instrument has been mounted to a teleoperated surgical system, which is in an activated state in FIG. 9. System installation indicator 556 may further include a second indicator 558 to display additional information about the teleoperated surgical system, such as which arm or manipulator the electrosurgical instrument has been mounted to. For instance, second indicator 558 may display a number to indicate which arm of a teleoperated surgical system that an electrosurgical instrument has been mounted to. In the event that an electrosurgical instrument has been mounted to a teleoperated surgical system but communication between an ESU and the instrument cannot be made, the second indicator 558 may indicate an error, as shown in the exemplary embodiment of FIG. 10. In such a situation, the ESU may be prevented from supplying a flux to the affected electrosurgical instrument.

The exemplary embodiments of ESUs discussed herein may provide flux to electrosurgical instruments mounted to a teleoperated surgical system and to electrosurgical instruments not mounted to a teleoperated surgical system, such as handheld instruments. The electrosurgical instruments may be smart electrosurgical instruments or conventional electrosurgical instruments that do not include "smart" technology. Further, the electrosurgical instruments may be activated, for example, by controls provided in a surgeon's console, such as console 150 in the exemplary embodiment of FIG. 1.

One type of control that may be used to activate an electrosurgical instrument is a foot pedal, which may part of a surgeon's console or a stand-alone switch (i.e., an auxiliary foot pedal not part of a surgeon's console 150). An auxiliary foot pedal may be used to activate a conventional electrosurgical instrument that does not include "smart" technology or to activate a smart electrosurgical instrument that is not mounted to a teleoperated surgical system. In view of this, an ESU may be configured so that the ESU is prevented from supplying a flux to a smart electrosurgical instrument mounted to a teleoperated surgical system when an auxiliary foot pedal is used to activate the instrument. Instead, other controls, such as finger switches of surgeon's console 150, may be used to activate a smart electrosurgical instrument when it is mounted to a teleoperated surgical system to minimize or prevent inadvertent activation of a surgical instrument mounted to a teleoperated surgical system via a foot pedal. Further, an ESU may be configured so that a foot pedal (of surgeon's console or auxiliary) may be assigned to only one module so that the foot pedal activates only one module and its associated electrosurgical instrument and not an additional module. A foot pedal may be switched in its assignment from one module to another, such as by using a toggle control of a teleoperated surgical system. According to an exemplary embodiment, an auxiliary foot pedal may be automatically assigned to the fourth module of an ESU by default (e.g., module 418 in FIG. 4), such as when a teleoperated surgical system includes three arms for three respective electrosurgical instruments.

Figure 11:
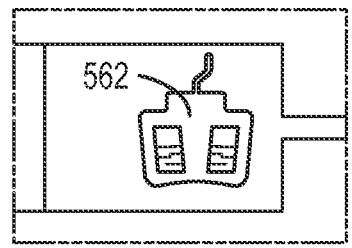
FIG. 11 is a front view of a foot pedal assignment indicator in an activated state, according to an exemplary embodiment.

An ESU module may display information indicating whether a module is assigned to a foot pedal, particularly an auxiliary foot pedal. As shown in the exemplary embodiment of FIG. 6, a module 460 may include a foot pedal assignment indicator 484, such as to indicate that module 460 is associated with an auxiliary foot pedal. FIG. 6 shows foot pedal assignment indicator 484 in a deactivated state, which informs a user that module 460 is not assigned to a foot pedal. FIG. 11 depicts a foot pedal assignment indicator 562 in an activated state to inform a user that a foot pedal, such as an auxiliary foot pedal, has been assigned to a particular module.

According to an exemplary embodiment, foot pedal assignment indicator 562 may display the number of available foot pedals. For instance, foot pedal assignment indicator 562 may display a single foot pedal (not shown) when a single foot pedal is used. According to an exemplary embodiment, a single foot pedal may be assigned to a module for a bipolar instrument, such as module 415 or 416 in the exemplary embodiment of FIG. 4. In another instance, foot pedal assignment indicator 562 may display a dual foot pedal, as shown in the exemplary embodiment of FIG. 11, when the foot pedal includes two switches. According to an exemplary embodiment, a dual foot pedal may be assigned to a module for a monopolar instrument, such as module 417 or 418 in the exemplary embodiment of FIG. 4. Regardless of the number of switches in a foot pedal (i.e., the foot pedal is a single foot pedal or a dual foot pedal), the foot pedal may be configured to activate only the module to which the foot pedal is associated, according to an exemplary embodiment. Further, a foot pedal may be configured to activate only particular types of modules, such as only a monopolar module or only a bipolar module. According to an exemplary embodiment, when a foot pedal includes a plurality of switches, such as a dual foot pedal, the different foot switches cannot be assigned to different energy modules, such as modules 417 and 418 in the exemplary embodiment of FIG. 4.

According to an exemplary embodiment, foot pedal assignment indicator 562 may include information about the operational state (i.e., mode) selected for the foot pedal. For instance, foot pedal assignment indicator 562 may provide a particular color, shape, or other indicator recognized by one of ordinary skill for the foot pedal shown in foot pedal assignment indicator 562 to indicate the operational state (i.e., mode) selected for that foot pedal. A first operational state (i.e., mode), such as a cut mode, may be indicated, for example, by coloring foot pedal a first color. A second operational state (i.e., mode), such as a coagulation or sealing function, may be indicated, for example, by coloring a foot pedal a second color different from the first color. If a foot pedal includes a plurality of switches, such as a dual foot pedal for a monopolar instrument, the different foot switches may include different indicators to inform a user of the selected operational states (i.e., modes) for the various switches. For instance, one foot switch may be colored a first color to indicate a first operational state (i.e., mode) and a second foot switch of the same dual foot pedal may be colored a second color different from the first color to indicate a second operational state (i.e., mode) different from the first mode in the foot pedal assignment indicator 562. The indicators provided in foot pedal assignment indicator 562 may correspond to the physical layout of the foot pedal when the foot pedal includes a plurality of switches. For instance, a switch on the left hand side of foot pedal assignment indicator 562 may include an indicator corresponding to the operational state (i.e., mode) for a foot switch on the left hand side of a foot pedal depressed by a user, while a switch on the right hand side of the pedal assignment indicator 562 may indicate an operational state (i.e., mode) for the right hand switch of the same foot pedal.

Figure 12:
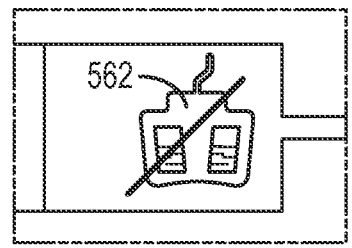
FIG. 12 is a front view of a foot pedal assignment indicator indicating an impermissible state, according to an exemplary embodiment.

According to an exemplary embodiment, a foot pedal assignment indicator may indicate to a user when a foot pedal has been impermissibly assigned to a module. Turning to FIG. 12, foot pedal assignment indicator 562 is shown in an activated state when a foot pedal has been impermissibly assigned to a module. A foot pedal may be impermissibly assigned to a module, for instance, when the electrosurgical instrument includes smart technology and is mounted to a teleoperated surgical system. In such a situation, the module that the foot pedal has been assigned to may be prevented from supplying a flux to the electrosurgical instrument until the foot pedal has been assigned to a different module.

As discussed above in regard to the exemplary embodiment of FIG. 1, when an ESU supplies flux to a monopolar electrosurgical instrument, a ground wire may couple the ESU to a patient. For instance, a patient may be coupled to an ESU via a grounding electrode 113, as described above with regard to the exemplary embodiment of FIG. 1. As shown in the exemplary embodiment of FIG. 4, an ESU may include a module 419 for the ground electrode, which may be connected to connector 424. Module 419 may also include a display screen section 444 to indicate the status of a ground electrode, as shown in FIG. 4.

Figure 13:
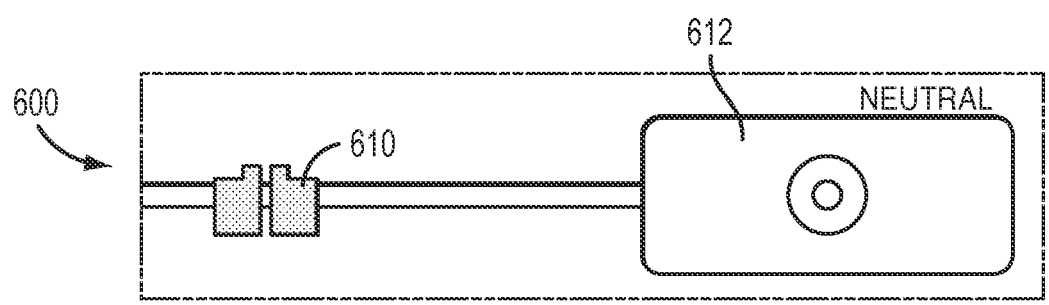
FIG. 13 is a front view of a module for a ground electrode indicating a connection with a ground electrode, according to an exemplary embodiment.
Figure 14:
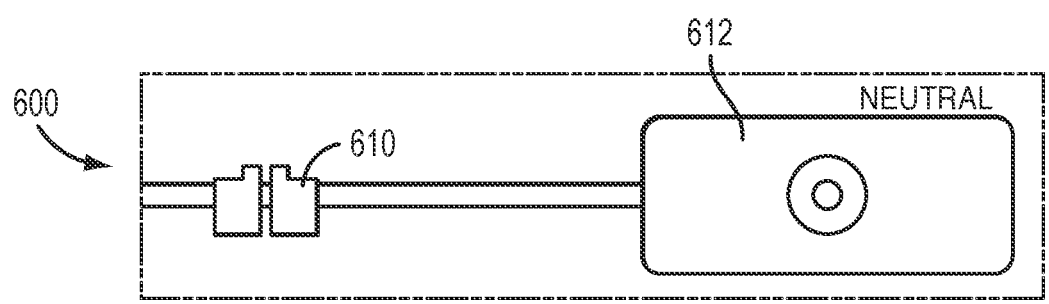
FIG. 14 is a front view of a module for a ground electrode indicating no connection with a ground electrode, according to an exemplary embodiment.

According to an exemplary embodiment, a display screen section of a ground electrode module of an ESU may indicate the connection status of the electrode. Turning to FIG. 13, an exemplary embodiment of a ground electrode module 600 for an ESU is shown that includes a connector 612 for connecting a ground electrode and a display screen section 610 to indicate a connection status of the electrode. In FIG. 13 the display screen section 610 is activated to indicate that a ground electrode is connected to connector 612. Display screen section 610 may, for example, activate by lighting up, changing color, flashing, and/or providing another visual indication of the connection status of the electrode. FIG. 14 shows the display screen section 610 in a deactivated state to indicate that a ground electrode is not connected to connector 612.

Figure 16:
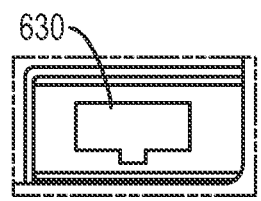
FIG. 16 is a front view of a display screen section for a ground electrode indicating no connection with a ground electrode having a single contact surface, according to an exemplary embodiment.

A ground electrode may, for example, be in the form of a pad having at least one electrically conductive surface that is connected to a ground wire. The pad may be in the form of a single surface or the pad may be split to provide dual contact surfaces, although a greater number of contact surfaces may be used. According to an exemplary embodiment, a display screen section of a ground electrode module may indicate the number of conductive surfaces of a ground electrode pad. A display screen section may indicate the number of contact surfaces numerically and/or visually, such as by providing a shape symbolizing the geometry of the pad. Turning to FIG. 15, an exemplary embodiment of a display screen section 620 for a ground electrode module is shown that indicates the use of a pad having two contact surfaces, wherein the pad is in a disconnected state. Conversely, FIG. 16 shows an exemplary embodiment of a display screen section 630 for a ground electrode module that indicates the use of a pad having a single contact surface in a disconnected state. According to an exemplary embodiment, when an indicator is in a deactivated state, the indicator may simply be unlit or not colored or the indicator may be colored or lit in way to provide a warning that a ground electrode is not connected, such as by being colored red.

Figure 17:
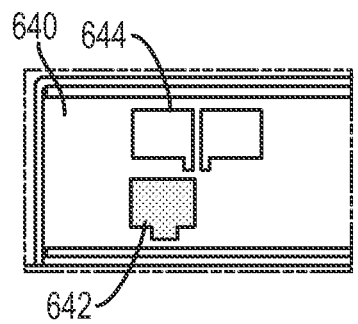
FIG. 17 is a front view of a display screen section configured to indicate a connection status for ground electrodes having various geometries, according to an exemplary embodiment.
Figure 18:
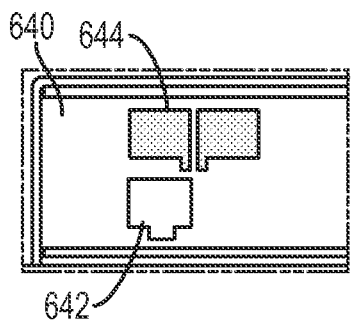
FIG. 18 is a front view of a display screen section configured to indicate a connection status for ground electrodes having various geometries, according to an exemplary embodiment.
Figure 19:
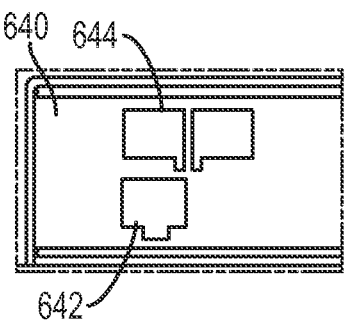
FIG. 19 is a front view of a display screen section configured to indicate a connection status for ground electrodes having various geometries, according to an exemplary embodiment.

According to an exemplary embodiment, a display screen section for a ground electrode module may be configured to indicate ground electrode pads having various geometries. Turning to FIG. 17, a display screen section 640 is shown that includes an indicator 642 for a pad having a single contact surface and an indicator 644 for a pad having two contact surfaces, with indicator 642 in an activated state and indicator 644 in a deactivated state. FIG. 18 shows the display screen section 640 with indicator 642 deactivated and indicator 644 activated. FIG. 19 shows the display screen section 640 with both indicators 642, 644 deactivated. As shown in FIG. 19, when both indicators 642, 644 are deactivated, indicators 642, 644 may both be lit or colored in a manner to indicate a warning to a user that neither electrode is connected, such as by being colored red.

According to an exemplary embodiment, an ESU may include one or more speakers (not shown) to generate audio tones, such as user feedback, warnings, and other audio output. For instance, the speakers may provide audible user feedback when an adjustment is made to a control setting or when a user attempts to perform an impermissible operation, such as making an impermissible connection to the ESU or adjust a setting beyond its minimum or maximum range. For instance, an ESU may provide an error tone when a foot pedal is impermissibly assigned to an electrosurgical instrument mounted to a teleoperated surgical system and/or when an attempt is made to use the foot pedal while it is impermissibly assigned.

Figure 20:
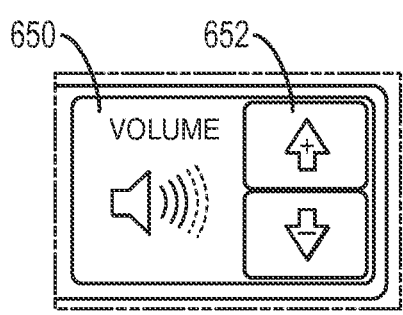
FIG. 20 is a front view of a volume indicator and a volume switch for an ESU, according to an exemplary embodiment.

As shown in the exemplary embodiment of FIG. 4, the display 412 may include a volume indicator 450 indicating a volume setting and a volume switch 452 configured to adjust the volume of audible output. FIG. 20 includes an enlarged view of a volume indicator 650 and volume switch 652 for a display of an ESU. According to an exemplary embodiment, volume indicator 450 may display the current volume setting on a numerical scale or may display the volume via a symbol or group of symbols. For instance, volume indicator 460 may indicate a volume setting via a number of lines, with a larger number of lines indicating a higher volume setting.

According to an exemplary embodiment, an ESU may be configured to store the settings of its various modules. For instance, a user may adjust the settings of one or more module(s) during use of an ESU and when the ESU is turned off the ESU stores the settings of each unit. When the ESU is turned back on, the setting can be restored. For instance, a user may select the stored settings or input new settings. In addition, the ESU may store the settings of a module when an electrosurgical instrument is disconnected from the module. For instance, if a user adjusts the settings of a module, disconnects an electrosurgical instrument from the module, adjusts the settings of the module while the electrosurgical instrument is disconnected, and reconnects the electrosurgical instrument, the ESU may restore the settings of the module to what the settings were just prior to the disconnection of the electrosurgical instrument.

Figure 21:
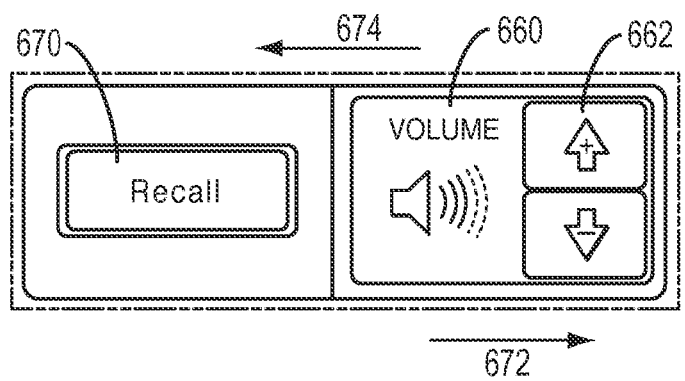
FIG. 21 is a front view of a recall button, volume indicator, and volume switch for an ESU, according to an exemplary embodiment.

Turning to FIG. 21, an exemplary embodiment of a recall button 670 is shown for a display of an ESU. A user may select recall button 670 to restore saved settings of ESU modules. According to an exemplary embodiment, recall button 670 may appear in the location of volume controls when an ESU is powered on. For instance, in the exemplary embodiment of FIG. 4, recall button 670 may appear in the location of volume indicator 450 and volume switch 452 when an ESU is turned on. When recall button 670 appears upon turning on an ESU, volume indicator 660 and volume switch 662 may be shifted to along direction 672 indicated in FIG. 21. Recall button 670 may, for example, remain on a display of an ESU until a user selects recall button 670, until the user adjusts the settings of a module without selecting recall button 670, or for a predetermined amount of time, such as, for example, 10 seconds or less. When recall button disappears, recall button 670, volume indicator 660, and volume switch 662 may shift in direction 674 shown in the exemplary embodiment of FIG. 21 so that recall button 670 is no longer visible.

Figure 22:
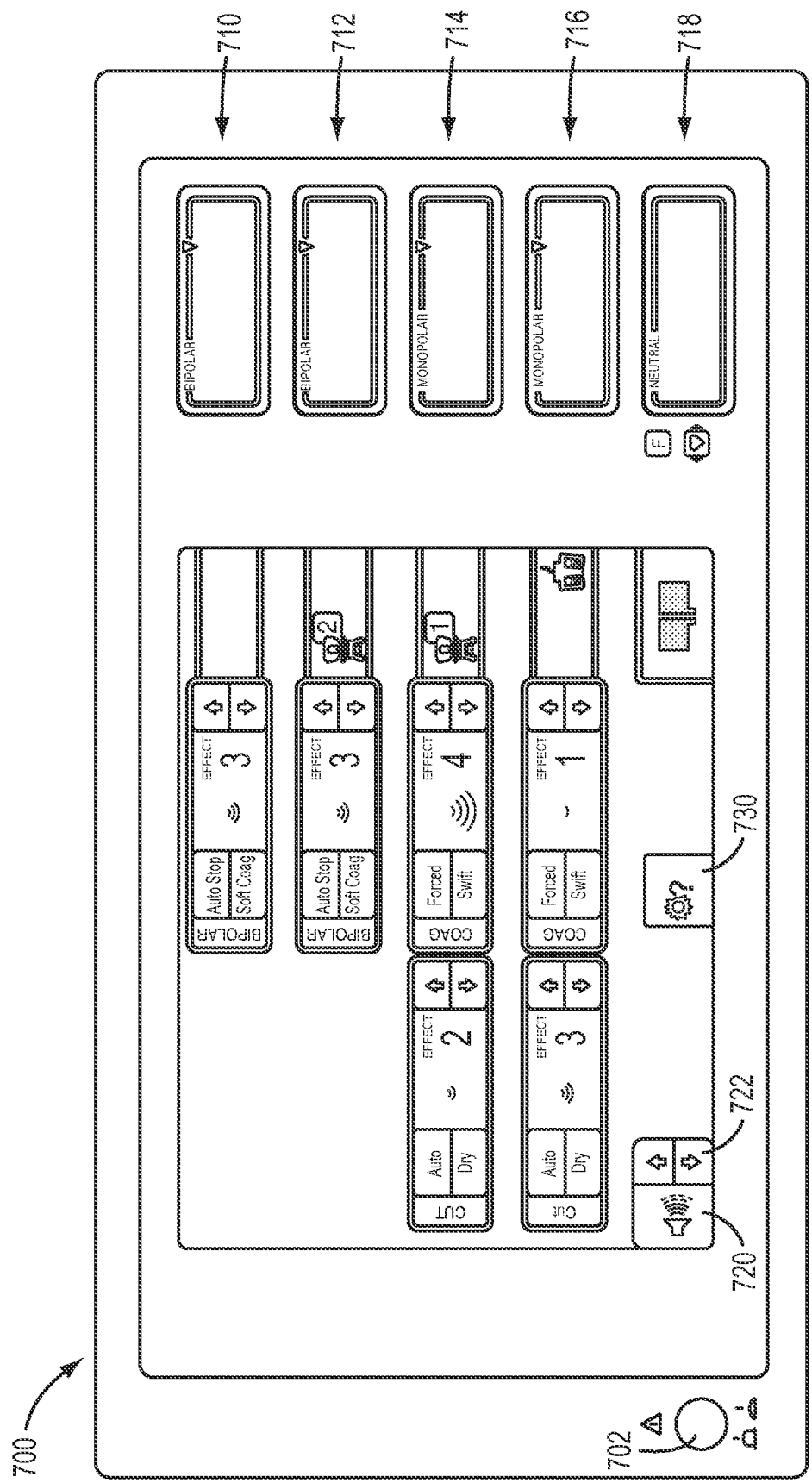
FIG. 22 is a front view of a display for an ESU that includes a button to access an administrative menu.

According to an exemplary embodiment, an ESU may include an administrative menu. An administrative menu may include, for example, diagnostic features, manuals, and/or other advanced functions not normally available to users. Turning to FIG. 22, an exemplary embodiment of a display 700 for an ESU is shown that includes a power button 702; modules 710, 712, 714, 716, 718; volume indicator 720; volume switch 722; and a button 730 to access the administrative menu. According to an exemplary embodiment, once button 730 is selected, a password may be required to access the administrative menu. According to another exemplary embodiment, a display may not include a button so that access to the administrative menu may be hidden. For instance, access to an administrative menu password prompt may be provided only when a user presses volume indicator 720 for a predetermined amount of time, such as for at least five seconds or other minimum set time period, for example.

As discussed above in the exemplary embodiments of FIGS. 4, 6, 23 and 24, display screen sections of a display and connectors may be arranged in a one-to-one relationship. In other words, for every individual display screen section a single connector is provided, or vice-versa. Thus, a single connector may be visually coupled with a single display screen section, as described above in the exemplary embodiments of FIGS. 4, 6, 23 and 24. However, the exemplary embodiments are not limited to such a relationship. According to an exemplary embodiment, a display screen section may be coupled with more than one connector for a surgical instrument, or vice versa. For instance, a display screen section may be coupled with two, three, or more connectors for surgical instruments. According to an exemplary embodiment, when a display screen section is coupled to a plurality of connectors, the plurality of connectors are for the same type of surgical instrument. For instance, the connectors may be for surgical instruments configured to receive the same flux type from a flux supply unit.

Figure 25:
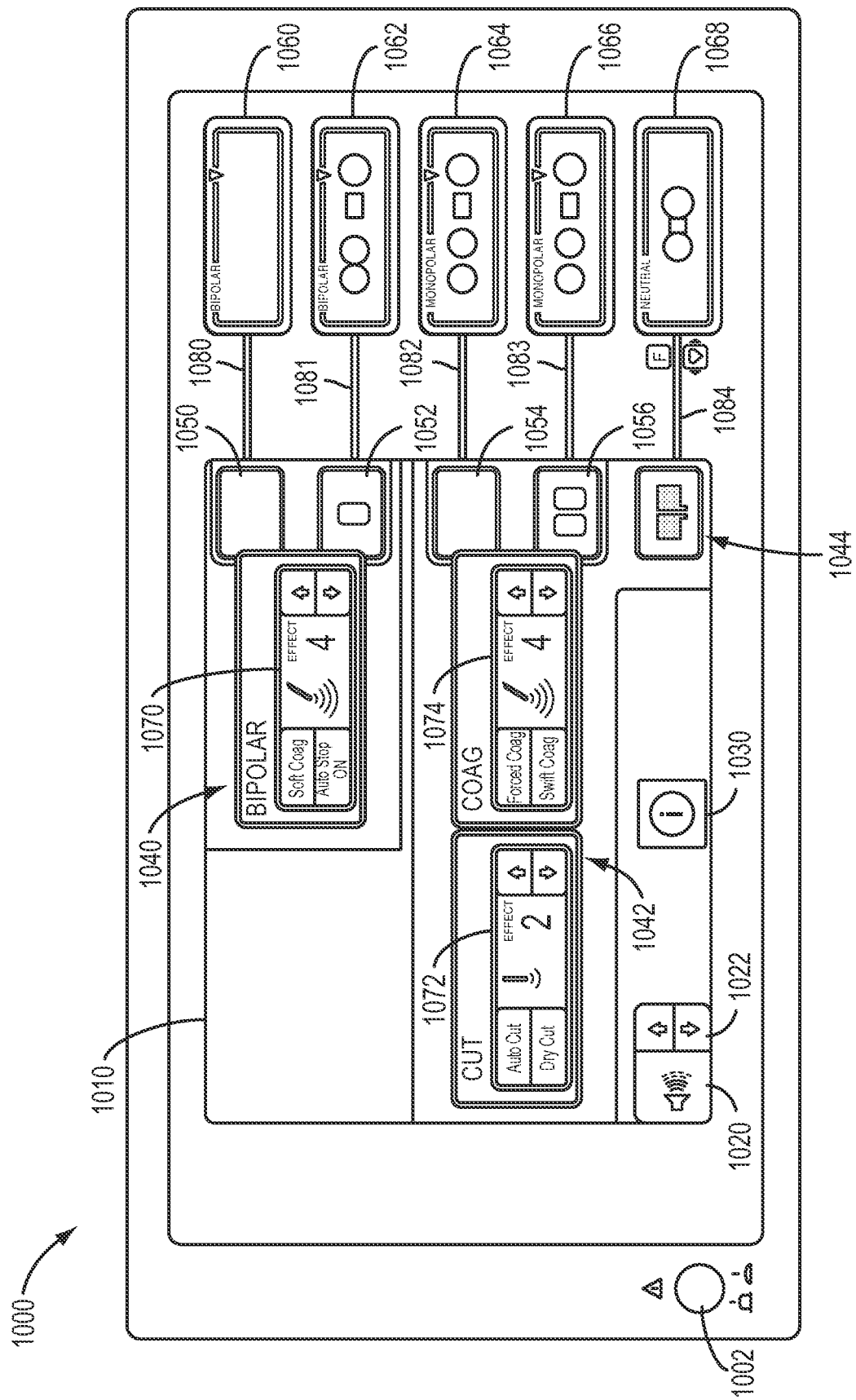
FIG. 25 is a front view of an exemplary embodiment of a user control interface and display of an ESU.

Turning to FIG. 25, an exemplary embodiment of an ESU user control interface 1000 is shown that includes a display 1010 and connectors 1060, 1062, 1064, 1066, 1068. Control interface 1000 may further include a power switch 1002, a volume indicator 1020, a volume switch 1022, and a button 1030 to access an administrative menu, as discussed above in the exemplary embodiments of FIGS. 4 and 22. Further, display 1010 may be partitioned into display screen sections 1040, 1042, 1044, as discussed above in the exemplary embodiments of FIGS. 4, 23, and 24. Display screen section 1044 and connector 1068 may be coupled to connector 1068 to provide a module for a ground electrode, as discussed above in the exemplary embodiments of FIGS. 4, 23, and 24. The display screen sections and connectors may be arranged horizontally, as shown in the exemplary embodiment of FIG. 25, or may be arranged in other manners to achieve visually coupling, such as, for example, according to the exemplary embodiments of FIGS. 23 and 24.

However, instead of individually visually coupling display screen sections 1040 and 1042 on a one-to-one basis with connectors 1060, 1062, 1064, 1066, connectors 1060 and 1062 may be visually coupled with display screen section 1040 and connectors 1064 and 1066 may be coupled with display screen section 1042. Thus, display screen section 1040 may include information for connectors 1060 and 1062 and display screen section 1042 may include information and controls for connectors 1064 and 1066.

Display screen sections 1040, 1042 may include mode display portions, as discussed above in the exemplary embodiments of FIGS. 4 and 6. For instance, display screen section 1040 may include, for example, a mode display portion 1070, such as for a bipolar mode of an instrument, and display screen section 1042 may include, for example, mode display portion 1072 and mode display portion 1074, such as for monopolar modes of an instrument. According to an exemplary embodiment, mode display portion 1070 may include information and controls for connectors 1060 and 1062 and mode display portions 1072, 1074 may include information and controls for connectors 1064 and 1066.

Further, mode display portion 1070 may be visually coupled to connectors 1060 and 1062 and mode display portions 1072, 1074 may be visually coupled to connectors 1064, 1066. For instance, mode display portion 1070 may be horizontally aligned with connectors 1060, 1062 so that a user visually scanning along mode display portion 1070 may easily find both connectors 1060, 1062. According to an exemplary embodiment, mode display portion 1070 may have a vertical height that overlaps with each of the vertical heights of connectors 1060 and 1062. Mode display portions 1072, 1074 may be similarly visually coupled to connectors 1064, 1066.

According to an exemplary embodiment, display screen sections may further include information sections configured to display various types of information about instruments connected to connectors coupled to the display screen sections. For instance, display screen section 1040 may include an information section 1050 configured to display information about an instrument connected to connector 1060 and an information section 1052 configured to display information about an instrument connected to connector 1062. Similarly, display screen section 1042 may include an information section 1054 configured to display information about an instrument connected to connector 1064 and an information section 1056 configured to display information about an instrument connected to connector 1066.

According to an exemplary embodiment, information sections may be visually coupled to connectors respectively associated with information sections. For instance, information sections may be individually visually coupled to connectors on a one-to-one basis. As shown in the exemplary embodiment of FIG. 25, information section 1050 may be individually visually coupled to connector 1060, information section 1052 may be individually visually coupled to connector 1062, information section 1054 may be individually visually coupled to connector 1064, and information section 1056 may be individually visually coupled to connector 1066. Information sections and connectors may be visually coupled in the same manner discussed for display screen sections and connectors discussed above in the exemplary embodiments of FIGS. 4, 23, and 24 and other arrangements that would be contemplated by those of ordinary skill in the art based on the present disclosure. For instance, information sections 1050, 1052, 1054, 1056 may have substantially the same respective vertical position as connectors 1060, 1062, 1064, 1066, may be substantially aligned along a same axis, may have substantially the same vertical height or horizontal width, and other techniques discussed above to provide visual coupling, which advantageously permits a user to easily determine which connector is associated with an information section, and vice versa. Further, display screen sections 1050, 1052, 1054, 1056 may be visually coupled with connectors 1060, 1062, 1064, 1066 by color. For instance, information sections 1050 and 1052 may have a common color with connector 1060. A common color may be provided, for example, in a border of the information sections and connectors, as a background color, or by other methods recognized by one of ordinary skill in the art. Further, information sections 1054 and 1056 may have a common color with connector 1062, which may be a second color different from the color used by information sections 1050, 1052 and connector 1060, and so on.

Further, information sections 1050, 1052, 1054, 1056 may visually couple mode display portions 1070, 1072, 1074 to connectors 1060, 1062, 1064, 1066. For instance, information sections 1050, 1052, 1054, 1056 may be individually visually coupled to connectors 1060, 1062, 1064, 1066, as discussed above, but may also be visually coupled to mode display portions 1070, 1072, 1074. Thus, information sections 1050, 1052 may serve as a bridge to visually couple mode display screen section 1070 to connectors 1060, 1062 and information sections 1054, 1056 may serve as a bridge to visually couple mode display portions 1072, 1074 to connectors 1064, 1066. According to an exemplary embodiment, interface 1000 may include additional features to visually couple display screen sections 1040, 1042 with connectors 1060, 1062, 1064, 1066. For instance, interface 1000 may include visual indicators 1080-1084, as discussed above in the exemplary embodiment of FIGS. 4, 23, and 24.

Information sections 1050, 1052, 1054, 1056 may provide various types of information about instruments connected to connectors 1060, 1062, 1064, 1066. For instance, information sections may indicate the source of activation of a mode, such as, for example, whether controls of a surgeon's console or a foot pedal is used to activate the ESU to provide a flux to an instrument. Information sections may indicate whether an instrument is a smart instrument, as discussed above in the exemplary embodiments of FIG. 6. Information sections may indicate whether an instrument is connected to a teleoperated surgical system and, if so, to which arm or manipulator the instrument is connected, as discussed above in the exemplary embodiments of FIGS. 6-10. Further, information sections may indicate whether a foot pedal is being used to activate the mode for an instrument, as discussed above in the exemplary embodiments of FIGS. 6, 11, and 12. In addition, if an information section indicates that a foot pedal is used to activate a mode for an instrument, information section may indicate which foot pedal is used if a plurality of foot pedals are provided.

Because interface 1000 includes mode display portions 1070, 1072, 1074 each visually coupled to a plurality of connectors 1060, 1062, 1064, 1066, the ESU for interface 1000 may include parameters to control activation of modes for instruments. According to an exemplary embodiment, if an instrument is connected to a teleoperated surgical system but an ESU cannot determine to which arm or manipulator the instrument is connected, the ESU will prevent the connector that the instrument is connected to from being activated, as well as other connectors visually coupled to that mode. For example, if an instrument connected to connector 1060 experiences this problem, connector 1060 and connector 1062 would be deactivated to minimize any confusion about which arm or manipulator has an instrument that is to be activated when a mode is used. Further, when a mode is activated, the corresponding mode display portion may indicate activation, as discussed above in the exemplary embodiment of FIG. 6. In addition, an information section corresponding to the connector for an instrument may also indicate activation in the same manner. For instance, if a mode is activated for an instrument connected to connector 1060, information section 1050 may indicate activation. In addition, mode display portion 1070 may also indicate activation, according to an exemplary embodiment.

As discussed above for the exemplary embodiment of FIG. 25, mode display portions may be visually coupled with multiple information sections and connectors. For instance, a display portion 1240 of the module 1200 of the exemplary embodiment of FIG. 26 may be visually coupled with information sections 1230, 1232 and connectors 1210, 1212. Display portion 1240 may be configured according to the display portions of the exemplary embodiment of FIG. 6. Display portion 1240 may also be visually coupled with visual indicators 1220, 1222. As a result, display portion 1240 may provide information and/or controls for instruments connected to connectors 1210 and 1212 because the instruments connected to connectors 1210 and 1212 would necessarily be the same type so that the same controls and parameters may be displayed in display portion 1240. However, some instruments are specialized and have specialized controls associated with them. An example of a specialized instrument is the da Vinci® Vessel Sealer, manufactured by Intuitive Surgical Inc. of Sunnyvale, Calif. According to an exemplary embodiment, when a specialized instrument (i.e., a smart instrument requiring specialized controls) is connected to a connector that shares a display portion with another connector (such as either of connectors 1210, 1212 in FIG. 26), the display portion coupled to the shared connectors may be reconfigured to provide specialized controls for the specialized instrument connector to one connector and standard controls for an instrument connected to the other connector. Turning to FIG. 27, module 1200 is shown after a specialized instrument (not shown) has been connected to connector 1210, resulting in mode display portion 1240 of FIG. 26 being reconfigured into mode display portion 1242 and mode display portion 1244 in FIG. 27. Mode display portion 1242 includes specialized controls and/or parameters (which may be saved within an ESU and loaded once a smart specialized instrument has been recognized or a user inputs the type of specialized instrument) and is visually coupled with information section 1250 and connector 1210. Mode display portion 1244 may include standardized controls and/or parameters (similar to mode display portion 1240) and is visually coupled with information section 1252 and connector 1212.

Figure 28:
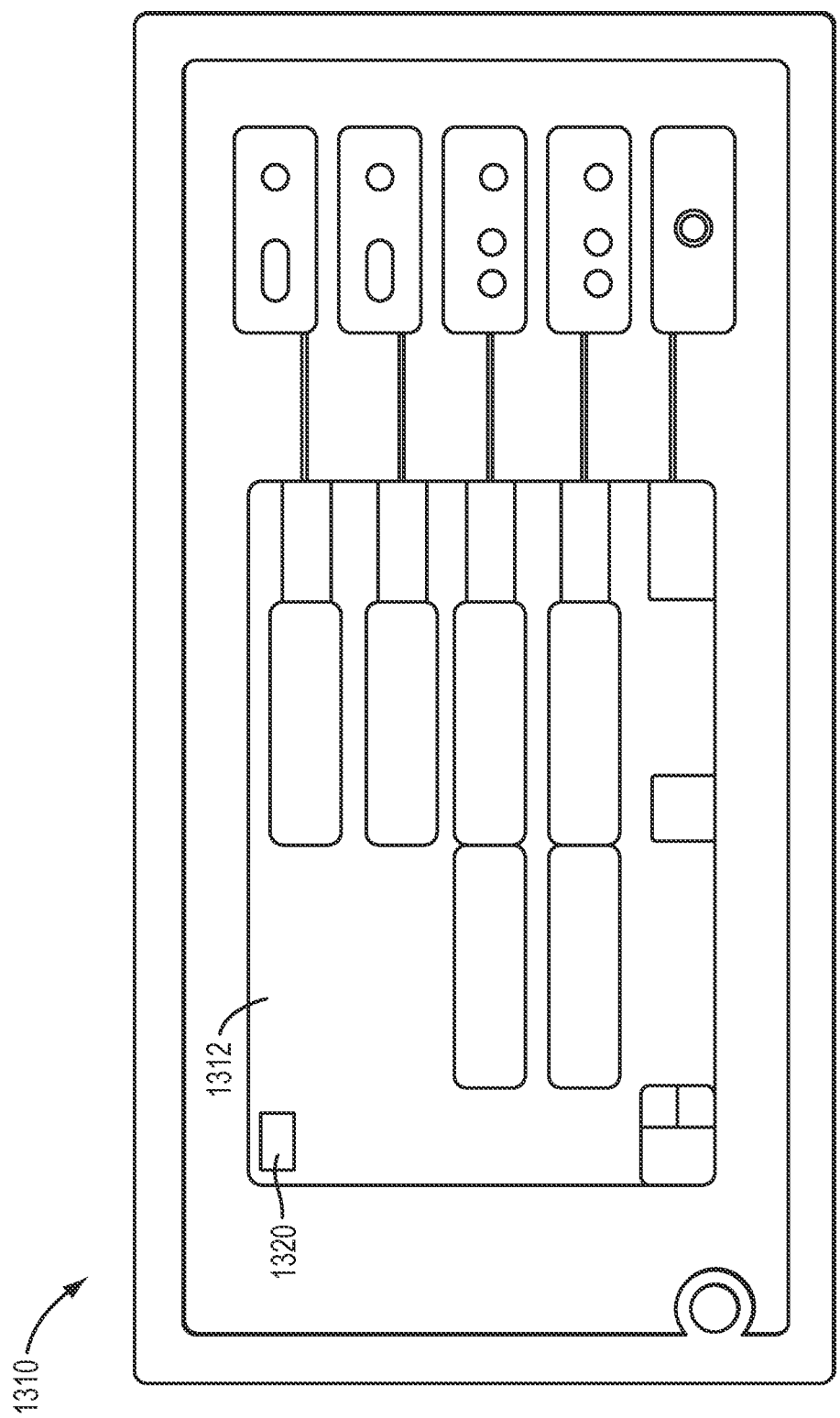
FIG. 28 is a front view of a display for an ESU that includes an icon to indicate a valid communication connection with a teleoperated surgical system.

A user control interface may include an icon to indicate a valid communication connection between an ESU and a teleoperated surgical system, such as the teleoperated surgical system 100A of the exemplary embodiment of FIG. 1. For example, the icon may indicate a valid communication connection between an ESU and any one of, or all of, control cart 150B, patient side cart 152, and/or surgeon's console 150. Turning to FIG. 28, an exemplary embodiment is shown of an ESU user control interface 1310 that includes a display 1312 including an icon 1320 indicating a valid communication connection between the ESU including user control interface 1310 and a teleoperated surgical system. According to an exemplary embodiment, when a valid communication connection is not present between the ESU and a teleoperated surgical system, icon 1320 may be absent. Icon 1320 may be used in combination with the various exemplary embodiments described herein.

By providing a flux supply unit, such as, for example, an ESU, with a display according to the embodiments described herein, a user may be provided with a variety of information about the flux supply unit and/or a surgical instrument, such as for example, an electrosurgical instrument, connected to the flux supply unit. Such information could be advantageously provided in a manner that is simple for a user to understand in a relatively short amount of time. Further, the flux supply unit may be arranged in a manner that is user-friendly and requires minimal or no training to use.

As discussed in the exemplary embodiments above, a display for an ESU or other flux supply unit may be provided by a touchscreen. Such a touchscreen may be responsive to a pressure applied to the touchscreen. For instance, a pressure may be applied to the touchscreen for a minimum time of about 5.4 milliseconds to initiate a response, which may occur within about 100 milliseconds. The touchscreen may be made of a scratch-resistant material and may have a diagonal size of about 13 inches or less, such as about 10.4 inches (about 264 mm) with a viewable area having a size of about 10×6 inches (about 254×152 mm), such as about 8.3×5.4 inches (about 212×138 mm). Further, the touchscreen may have a minimum resolution of, for example, about 800×600 pixels and have a minimum frame rate of about 24 frames per second.

Exemplary embodiments, including the various operational methods described herein, can be implemented in computing hardware (computing apparatus) and/or software, such as (in a non-limiting example) any computer that can store, retrieve, process and/or output data and/or communicate with other computers. The results produced can be displayed on a display of the computing hardware. One or more programs/software comprising algorithms to affect the various responses and signal processing in accordance with various exemplary embodiments of the present disclosure can be implemented by a processor, such as data interface module, of or in conjunction with the control cart including core processor and may be recorded on computer-readable media including computer-readable recording and/or storage media. Examples of the computer-readable recording media include a magnetic recording apparatus, an optical disk, a magneto-optical disk, and/or a semiconductor memory (for example, RAM, ROM, etc.). Examples of the magnetic recording apparatus include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

This description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Further, the term "immediate" may mean a response that occurs within a time period of, for example, less than or equal to about 100 ms.

It is to be understood that the particular examples and embodiments set forth herein are nonlimiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with a true scope and spirit being indicated by the following claims.

What is claimed is:

1. A method, comprising:
    receiving, at a single display screen of a flux supply unit, input at one or both of a first control of a first graphical user interface section and a second control of a second graphical user interface section, wherein:

the first graphical user interface section of the display screen aligns along a first axis with a first connector port configured to be operably coupled to a surgical instrument, the first graphical user interface section comprising a first indicator extending along the first axis and providing a visual association between the first graphical user interface section and the first connector port, the second graphical user interface section of the display screen aligns along a second axis with a second connector port configured to be operably coupled to a surgical instrument, the second graphical user interface section comprising a second indicator extending along the second axis and providing a visual association between the second graphical user interface section and the second connector port, and the first graphical user interface section and the second graphical user interface section are simultaneously available to receive input at the display screen;

adjusting an appearance of one or both of the first indicator and the second indicator in response to a respective surgical instrument in a connected state with one or both of the first connector port or the second connector port comprising a storage device storing information about the respective surgical instrument; and adjusting an output of one or both of the first connector port and the second connector port based on the input.

2. The method of claim 1, further comprising one or both of:
displaying a third indicator on the first graphical user interface section to indicate that an electrosurgical instrument is operably coupled to the first connector port, and
displaying a fourth indicator on the second graphical user interface section to indicate that an electrosurgical instrument is operationally coupled to the second connector port.

3. The method of claim 2, wherein a surgical instrument is operably coupled to the first connector port, and the method further comprises:
displaying a fifth indicator on the first graphical user interface section to indicate to which arm of a manipulator system of a surgical system the surgical instrument is mounted.

4. The method of claim 1, further comprising:
transmitting information about the respective surgical instrument stored on the storage device from the storage device to the flux supply unit; and
adjusting the output of one or both of the first connector port and the second connector port based on the information about the respective surgical instrument.

5. The method of claim 1, wherein:
a first user input mechanism is operably coupled to control an output at the first connector port, and
the method further comprises displaying a third indicator at the first graphical user interface section, the third indicator indicating the first user input mechanism is operably coupled to control the output at the first connector port.

6. The method of claim 5, wherein:
a second user input mechanism is operably coupled to control an output at the second connector port, and
the method further comprises displaying a fourth indicator at the second graphical user interface section, the fourth indicator indicating the second user input mechanism is operably coupled to control the output at the second connector port.

7. The method of claim 1, further comprising displaying, on the single display screen, an icon indicating a status regarding a state of signal communication between the flux supply unit and a surgical system to which the flux supply unit is operably coupled.

8. The method of claim 1, further comprising graphically partitioning the single display screen into the first graphical user interface section and second graphical user interface section.

9. The method of claim 8, wherein graphically partitioning comprises providing a border around each of the first and second graphical user interface sections.

10. The method of claim 8, wherein graphically partitioning comprises providing space between each of the first and second graphical user interface sections.

11. The method of claim 1, further comprising changing an appearance of one or both of the first and second graphical user interface sections based on a type of flux a surgical instrument operably coupled to one or both of the first or second connector ports is configured to receive.

12. The method of claim 1, further comprising one or both of:
displaying on the first graphical user interface section information regarding a first surgical instrument coupled with the first connector port; and
displaying on the second graphical user interface section information regarding a second surgical instrument coupled with the second connector port.

13. The method of claim 12, wherein the information comprises one or more of a type of flux the surgical instrument is configured to receive, instrument settings, flux supply unit settings, and connection state of the at least one first and second surgical instrument.

14. The method of claim 12, wherein:
displaying on the first graphical user interface section information regarding the first surgical instrument comprises displaying a monopolar mode or a bipolar mode of the first surgical instrument, and
displaying on the second graphical user interface section information regarding the second surgical instrument comprises displaying a monopolar mode or a bipolar mode of the second surgical instrument.

15. The method of claim 1, wherein the first and second graphical user interface sections comprise adjustable control setting icons to respectively control output at each of the first and second connector ports.

16. The method of claim 1, further comprising, prior to receiving input at one or both of a first control of a first graphical user interface section and a second control of a second graphical user interface section:
displaying the first graphical user interface section on the display screen based on operable connection of a first surgical instrument to the first connector port, and
displaying the second graphical user interface section on the display screen based on operable connection of a second surgical instrument to the second connector port.

17. The method of claim 1, wherein adjusting an appearance of one or both of the first indicator and the second indicator comprises one or both of adjusting an illumination of one or both of the first indicator and second indicator and adjusting a color of one or both of the first indicator and the second indicator.

18. The method of claim 1, wherein:
the first axis and the second axis are parallel to one another, the first graphical user interface section is adjacent to the first connector port, and the second graphical user interface section is adjacent the second connector port.

* * * * *